(12) United States Patent
Bingham

(10) Patent No.: US 10,126,122 B2
(45) Date of Patent: Nov. 13, 2018

(54) ULTRASONIC INSPECTION OF WRINKLES IN COMPOSITE OBJECTS

(71) Applicant: The Boeing Company, Chicago, IL (US)

(72) Inventor: Jill Paisley Bingham, Seattle, WA (US)

(73) Assignee: The Boeing Company, Chicago, IL (US)

( * ) Notice: Subject to any disclaimer, the term of this patent is extended or adjusted under 35 U.S.C. 154(b) by 229 days.

(21) Appl. No.: 15/098,765

(22) Filed: Apr. 14, 2016

(65) Prior Publication Data

US 2017/0299381 A1 Oct. 19, 2017

(51) Int. Cl.
| | |
|---|---|
| *G01N 29/04* | (2006.01) |
| *G01N 29/06* | (2006.01) |
| *G01N 29/44* | (2006.01) |
| *G01N 29/26* | (2006.01) |
| *G01B 17/00* | (2006.01) |

(52) U.S. Cl.
CPC ............. *G01B 17/00* (2013.01); *G01N 29/04* (2013.01); *G01N 29/043* (2013.01); *G01N 29/069* (2013.01); *G01N 29/262* (2013.01); *G01N 29/44* (2013.01); *G01N 2291/01* (2013.01); *G01N 2291/0231* (2013.01); *G01N 2291/0289* (2013.01); *G01N 2291/02854* (2013.01); *G01N 2291/044* (2013.01); *G01N 2291/103* (2013.01); *G01N 2291/106* (2013.01); *G01N 2291/2694* (2013.01)

(58) Field of Classification Search
CPC ...... G01F 1/663; G01P 5/001; G01S 15/8918; G01S 15/8984; G01S 15/8913
USPC ........................................................ 73/628
See application file for complete search history.

(56) References Cited

U.S. PATENT DOCUMENTS

| | | | |
|---|---|---|---|
| 5,280,724 A | 1/1994 | Higo et al. | |
| 5,398,216 A * | 3/1995 | Hall | ........................ G01F 1/663 367/90 |
| 5,431,054 A | 7/1995 | Reeves et al. | |

(Continued)

FOREIGN PATENT DOCUMENTS

| | | |
|---|---|---|
| DE | 102011108730 A1 | 1/2013 |
| EP | 2472254 A2 | 7/2012 |
| EP | 2653829 A1 | 10/2013 |

OTHER PUBLICATIONS

Georgeson et al., "Quantification of Wrinkles in Composite Objects," U.S. Appl. No. 14/049,974, filed Oct. 9, 2013, 45 pages.

(Continued)

*Primary Examiner* — J M Saint Surin
(74) *Attorney, Agent, or Firm* — Yee & Associates, P.C.

(57) ABSTRACT

A method and apparatus for evaluating an object having a wrinkle are provided. An array of receiving elements is configured such that only two receiving apertures are configured to receive at a given point in time. Energy is sent into the object using an array of transmitting elements. Reflected energy is received at the only two receiving apertures of the array of receiving elements in response to a portion of the energy being reflected off a plurality of layers in the object. A number of dimensions of a wrinkle in the object is determined based on the reflected energy received at the only two receiving apertures of the array of receiving elements.

17 Claims, 13 Drawing Sheets

(56) References Cited

U.S. PATENT DOCUMENTS

| | | | |
|---|---|---|---|
| 5,554,808 A * | 9/1996 | Chiao | G01N 29/07 |
| | | | 73/598 |
| 5,637,799 A | 6/1997 | Hayman et al. | |
| 5,992,235 A | 11/1999 | Fischer et al. | |
| 6,070,466 A | 6/2000 | Taran et al. | |
| 9,575,033 B1 * | 2/2017 | Georgeson | G01N 29/07 |
| 2012/0219034 A1 | 8/2012 | Nielsen | |
| 2013/0031979 A1 * | 2/2013 | Bergman | G01N 29/043 |
| | | | 73/599 |
| 2013/0088222 A1 * | 4/2013 | Nissen | G01N 27/9046 |
| | | | 324/240 |

OTHER PUBLICATIONS

Extended European Search report, dated Aug. 8, 2017, regarding Application No. 17165793.5, 9 pages.

* cited by examiner

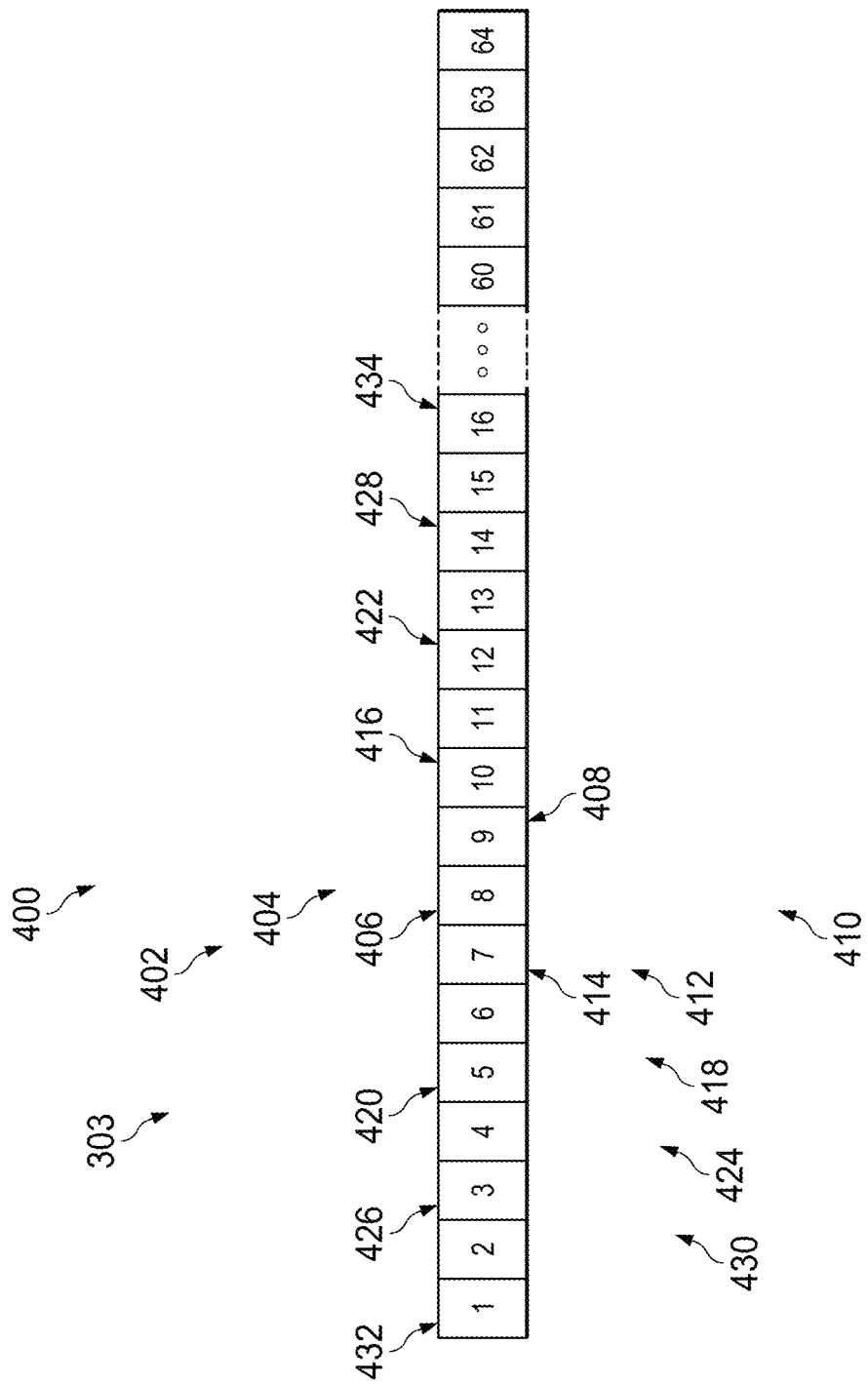

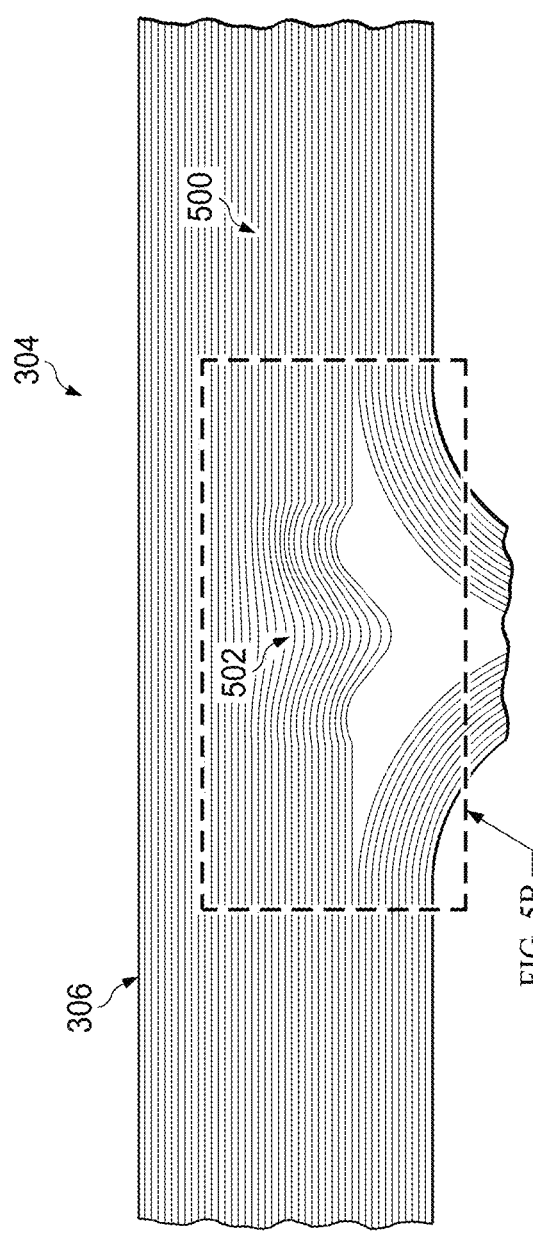
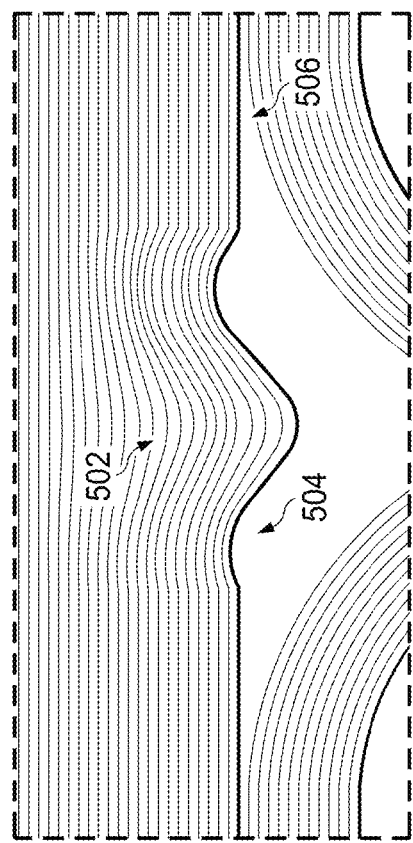

ULTRASONIC INSPECTION OF WRINKLES IN COMPOSITE OBJECTS

BACKGROUND INFORMATION

1. Field

The present disclosure relates generally to wrinkles in composite objects and, in particular, to evaluating the wrinkles in the composite objects. Still more particularly, the present disclosure relates to a method and apparatus for determining a number of dimensions of a wrinkle in a composite object using an ultrasonic inspection system.

2. Background

A composite object may be comprised of multiple layers. These layers are oftentimes referred to as composite plies. In some cases, a wrinkle may form within a composite object. The wrinkle may be formed by a ridge, a furrow, and/or a crease in one or more layers of a portion of the composite object. The wrinkle in the composite object may reduce one or more of the mechanical properties of the composite object. For example, without limitation, a wrinkle may reduce the stiffness of a composite object at or near the location of the wrinkle.

Different types of inspection systems may be used to detect wrinkles in composite objects. For example, an ultrasonic inspection system may be used to identify a wrinkle in a composite object. However, some currently available ultrasonic inspection systems may be unable to quantify certain properties about a wrinkle in a composite object. As one illustrative example, some currently available ultrasonic inspection systems may be unable to measure the actual shape or size of a wrinkle. In particular, these ultrasonic inspection systems may be unable to measure the width of a wrinkle in a composite object.

The shape and size of a wrinkle in a composite object may determine how the wrinkle affects the mechanical properties of the composite object. When the shape and size of a wrinkle in a composite object cannot be quantified, the wrinkle may need to be assumed as a "worst-case" scenario. The composite object may then need to be discarded or reworked even if the wrinkle actually has a shape and size within selected tolerances. Therefore, it would be desirable to have a method and apparatus that take into account at least some of the issues discussed above, as well as other possible issues.

SUMMARY

In one illustrative example, a method is provided. An array of receiving elements is configured such that only two receiving apertures are configured to receive at a given point in time. Energy is sent into the object using an array of transmitting elements. Reflected energy is received at the only two receiving apertures of the array of receiving elements in response to a portion of the energy being reflected off a plurality of layers in the object. A number of dimensions of a wrinkle in the object is determined based on the reflected energy received at the only two receiving apertures of the array of receiving elements.

In another illustrative example, an apparatus comprises an array of transmitting elements, an array of receiving elements, and a processor unit. The array of transmitting elements is configured to send energy to a plurality of locations on an object. The array of receiving elements has only two receiving apertures configured to receive at least a portion of the energy that is reflected off the object as reflected energy. The processor unit is configured to determine a width of a wrinkle in the object based on the reflected energy.

In yet another illustrative example, a method is provided. An array of elements is configured such that only a pair of receiving apertures is configured to receive at a given point in time. The array of elements is configured such that a transmitting aperture is substantially centered between the pair of receiving apertures of the array of elements. Energy is sent into an object using the transmitting aperture. Reflected energy is received at the pair of receiving apertures in response to a portion of the energy being reflected off a plurality of layers in the object.

The features and functions can be achieved independently in various examples of the present disclosure or may be combined in yet other examples in which further details can be seen with reference to the following description and drawings.

BRIEF DESCRIPTION OF THE DRAWINGS

The novel features believed characteristic of the illustrative examples are set forth in the appended claims. The illustrative examples, however, as well as a preferred mode of use, further objectives and features thereof, will best be understood by reference to the following detailed description of an illustrative example of the present disclosure when read in conjunction with the accompanying drawings, wherein:

FIG. 4 is an illustration of a layout of receiving apertures in an array of elements in accordance with an illustrative example;

FIGS. 5A and 5B are illustrations of a cross-sectional view of a composite object in accordance with an illustrative example;

DETAILED DESCRIPTION

The illustrative examples recognize and take into account different considerations. For example, the illustrative examples recognize and take into account that it may be desirable to have a method and apparatus capable of quantifying a number of dimensions of a wrinkle in a composite object. The number of dimensions includes at least one of the width of the wrinkle or the depth of the wrinkle. The illustrative examples recognize and take into account that a phased array ultrasonic inspection system may be used to determine the width of the wrinkle.

Further, the illustrative examples recognize and take into account that the layers of a composite object may be arranged substantially parallel to a plane. However, when a wrinkle is present in a portion of the composite object, one or more of the layers of the composite object may be raised or lowered outside this plane. In this manner, the wrinkle may be referred to as an "out-of-plane" wrinkle.

The illustrative examples recognize and take into account that a phased array ultrasonic inspection system may be used to determine if the wrinkle is of acceptable quality. For instance, the illustrative examples recognize and take into account that at least one of the width of the wrinkle or the out-of-plane angles of the layers in the wrinkle may affect the quality of composite object. The illustrative examples recognize and take into account that a phased array ultrasonic inspection system may be used to determine if the out-of-plane angles of the layers of the composite object are above a threshold.

The illustrative examples recognize and take into account that the out-of-plane angles of the layers of the composite object influence a direction of reflected energy. For example, the illustrative examples recognize and take into account that the out-of-plane angles of the layers of the composite object preferentially direct the amplitude of reflected energy.

Figure 1:
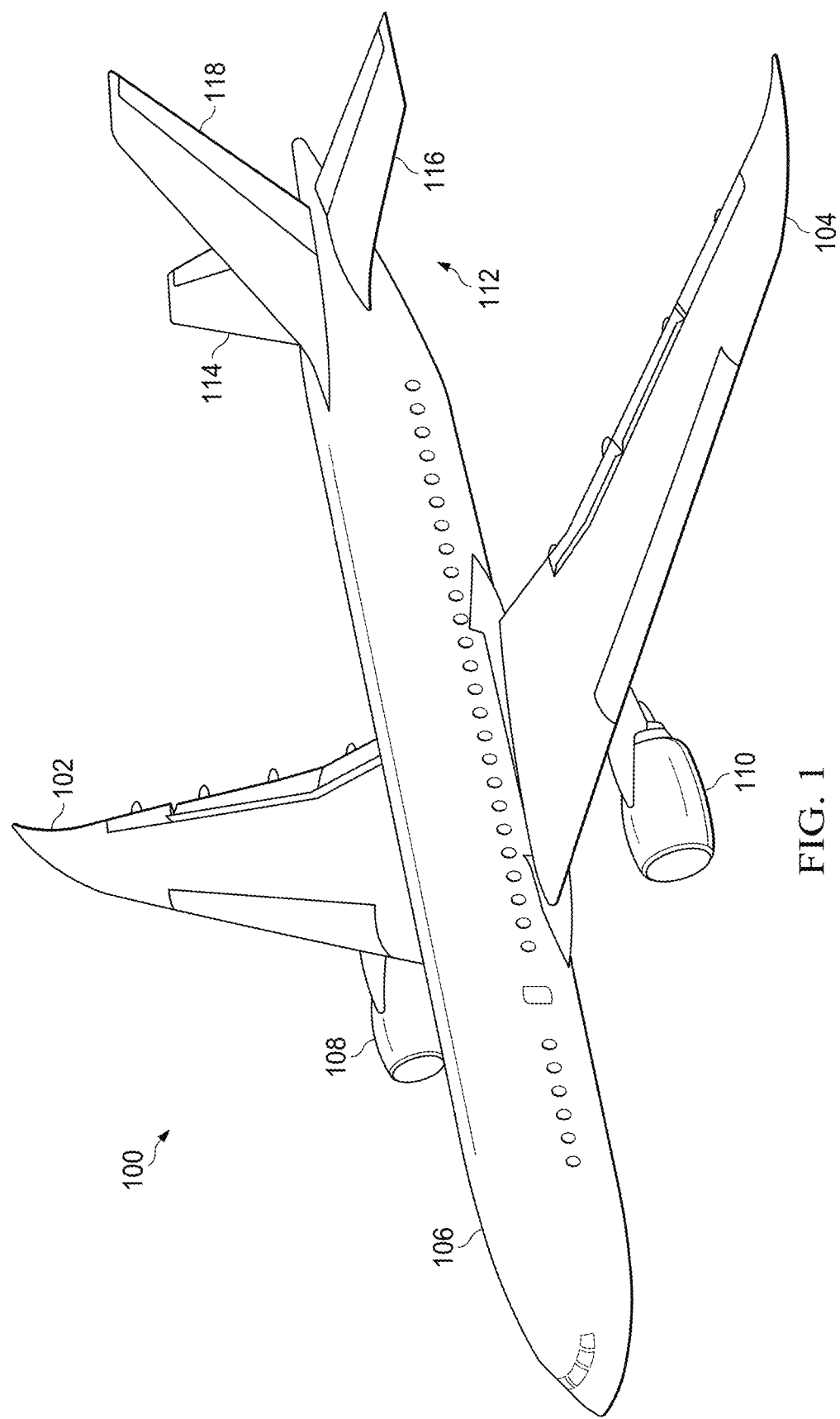
FIG. 1 is an illustration of an aircraft in which an illustrative example may be implemented.

Referring now to the figures and, in particular, with reference to FIG. 1, an illustration of an aircraft is depicted in which an illustrative example may be implemented. In this illustrative example, aircraft 100 has wing 102 and wing 104 attached to body 106. Aircraft 100 includes engine 108 attached to wing 102 and engine 110 attached to wing 104. Body 106 has tail section 112. Horizontal stabilizer 114, horizontal stabilizer 116, and vertical stabilizer 118 are attached to tail section 112 of body 106.

Aircraft 100 is an example of an aircraft having composite structures that may be inspected with an ultrasound inspection system in accordance with an illustrative example. For example, composite skin in at least one of wing 102 or wing 104 may be inspected using an ultrasound inspection system to determine characteristics of wrinkles.

As used herein, the phrase "at least one of," when used with a list of items, means different combinations of one or more of the listed items may be used, and only one of each item in the list may be needed. In other words, "at least one of" means any combination of items and number of items may be used from the list, but not all of the items in the list are required. The item may be a particular object, thing, or a category.

For example, "at least one of item A, item B, or item C" may include, without limitation, item A, item A and item B, or item B. This example also may include item A, item B, and item C or item B and item C. Of course, any combinations of these items may be present. In other examples, "at least one of" may be, for example, without limitation, two of item A; one of item B; and ten of item C; four of item B and seven of item C; or other suitable combinations.

This illustration of aircraft 100 is provided for purposes of illustrating one environment in which the different illustrative examples may be implemented. The illustration of aircraft 100 in FIG. 1 is not meant to imply architectural limitations as to the manner in which different illustrative examples may be implemented. For example, aircraft 100 is shown as a commercial passenger aircraft. The different illustrative examples may be applied to other types of aircraft, such as a private passenger aircraft, a rotorcraft, or other suitable types of aircraft.

Although the illustrative examples for an illustrative example are described with respect to an aircraft, an illustrative example may be applied to other types of platforms. The platform may be, for example, a mobile platform, a stationary platform, a land-based structure, an aquatic-based structure, or a space-based structure. More specifically, the platform may be a surface ship, a tank, a personnel carrier, a train, a spacecraft, a space station, a satellite, a submarine, an automobile, a manufacturing facility, a building, or other suitable platforms.

Further, an illustrative example may be applied to other types of composite structures. For example, composite structures other than platforms may be inspected using a laser ultrasound inspection system. Composite structures other than platforms may include medical devices, prosthetic limbs, or any other desirable products for the screening, diagnosis, treatment, prevention or any combination or sub-combination thereof of physical or mental health conditions in human beings or animals.

Figure 2:
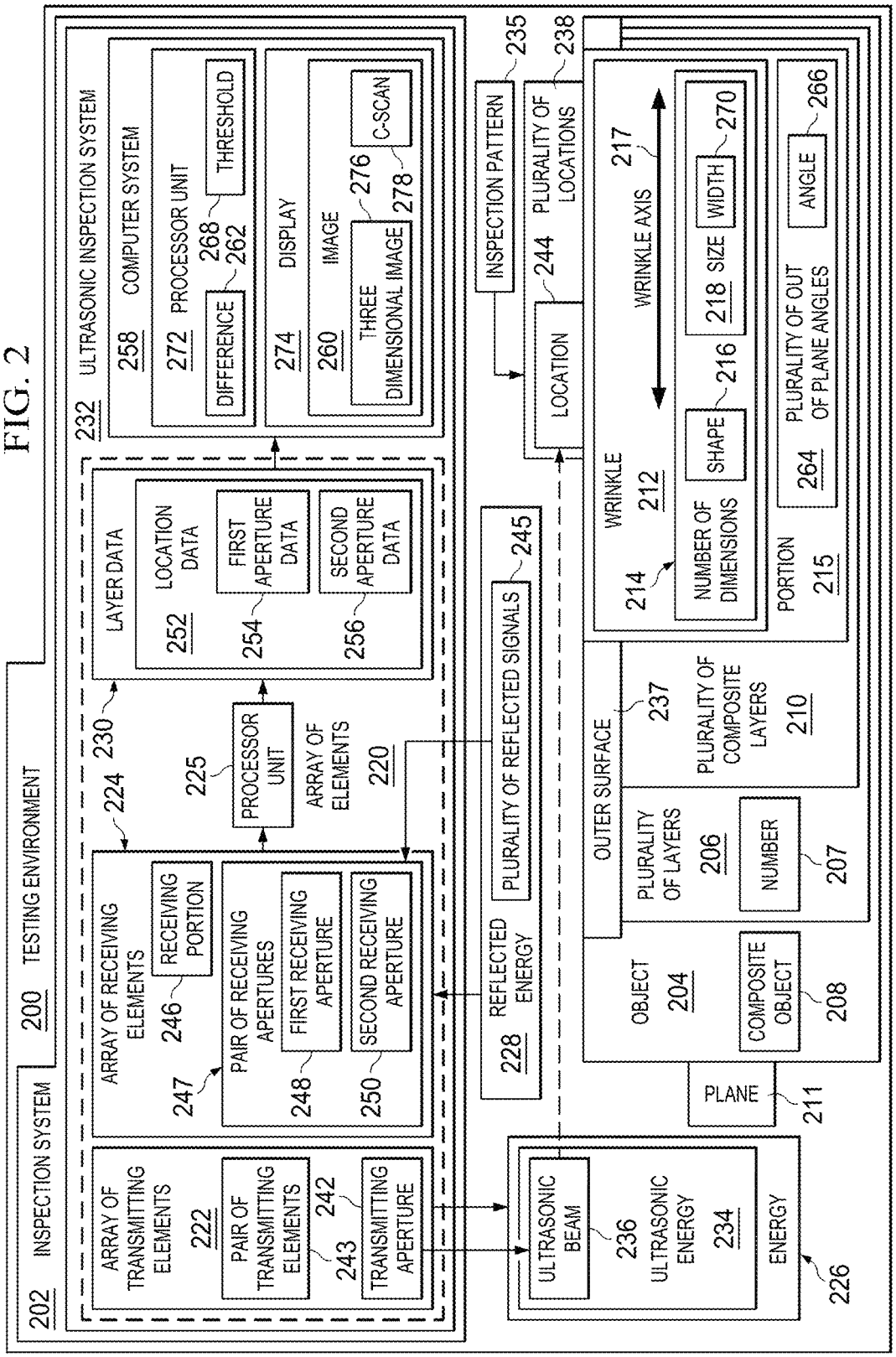
FIG. 2 is an illustration of a testing environment in the form of a block diagram in accordance with an illustrative example.

With reference now to FIG. 2, an illustration of a testing environment is depicted in the form of a block diagram in accordance with an illustrative example. In this illustrative example, testing environment 200 is an environment in which inspection system 202 is used to evaluate object 204.

As depicted, object 204 is any desirable object comprised of plurality of layers 206. Number 207 is the number of layers in plurality of layers 206. In one illustrative example, object 204 takes the form of composite object 208. When object 204 is composite object 208, plurality of layers 206 may be referred to as plurality of composite layers 210. In these examples, object 204 is composite object 208 comprised of plurality of composite layers 210. Plurality of composite layers 210 may also be referred to as a plurality of plies or composite plies in some cases. Each of plurality of composite layers 210 may be comprised of composite material.

In one illustrative example, object 204 is substantially planar. In this example, plurality of layers 206 that forms object 204 is arranged substantially parallel to plane 211. However, in some cases, wrinkle 212 may be present or develop within object 204. Wrinkle 212 may be formed by, for example, a ridge, a furrow, and/or a crease in one or more of plurality of layers 206.

Inspection system 202 is used to evaluate wrinkle 212. In particular, inspection system 202 is used to quantify number of dimensions 214 of wrinkle 212. For example, number of dimensions 214 includes one or more properties of wrinkle 212. In this illustrative example, number of dimensions 214 includes shape 216 and size 218 of wrinkle 212.

In one illustrative example, a different type of inspection system is first used to identify portion 215 of object 204 that includes wrinkle 212 and identify wrinkle axis 217. Portion 215 of object 204 identified may depend on shape 216 and size 218 of wrinkle 212. Portion 215 may be identified such that portion 215 includes all of wrinkle 212 as well as some of the unwrinkled portion of object 204 around wrinkle 212.

In another illustrative example, the speed of inspection system 202 may allow for inspection of all of object 204 for wrinkle 212. In this illustrative example, a different type of inspection system is not used to identify portion 215 of object 204. Accordingly, use of inspection system 202 may reduce total inspection time for object 204. Further, use of inspection system 202 may reduce the cost for inspecting object 204.

Wrinkle 212 extends substantially linearly, within tolerances, in a direction substantially parallel to plane 211. Wrinkle axis 217 is identified as the axis in the direction in which wrinkle 212 extends.

Inspection system 202 is used to inspect portion 215 of object 204 to quantify shape 216 and size 218 of wrinkle 212. As depicted, inspection system 202 includes array of transmitting elements 222, array of receiving elements 224, and processor unit 225. In some cases, array of transmitting elements 222 and array of receiving elements 224 are implemented as separate arrays. However, in other cases, array of transmitting elements 222 and array of receiving elements 224 are implemented as a same array of elements 220. In these cases, array of elements 220 is configured for use in both transmitting and receiving. In some examples, array of elements 220 is implemented as an array of transducers.

In this illustrative example, array of transmitting elements 222 includes two or more elements arranged in a row. In this example, array of transmitting elements 222 is a linear array of transmitting elements. Similarly, array of receiving elements 224 includes two or more elements arranged in a row. In this example, array of receiving elements 224 is a linear array of receiving elements.

Array of transmitting elements 222 is configured to send energy 226 into object 204. Array of receiving elements 224 is configured to receive reflected energy 228. Reflected energy 228 is the portion of energy 226 sent into object 204 that is reflected off the surface of each of plurality of layers 206.

In one illustrative example, inspection system 202 takes the form of ultrasonic inspection system 232. When inspection system 202 takes the form of ultrasonic inspection system 232, energy 226 sent into object 204 is ultrasonic energy 234.

Ultrasonic inspection system 232 is placed over outer surface 237 of portion 215 of object 204. In this illustrative example, ultrasonic inspection system 232 is placed over outer surface 237 such that array of transmitting elements 222 directly contacts outer surface 237. However, in other illustrative examples, ultrasonic inspection system 232 is placed over outer surface 237 such that array of transmitting elements 222 does not directly contact outer surface 237. This distance may be referred to as standoff. Standoff from outer surface 237 of composite object 208 may be related to the thickness of composite object 208.

Ultrasonic inspection system 232 is then operated to send ultrasonic energy 234 into object 204 at plurality of locations 238 on outer surface 237 of portion 215 of object 204. More specifically, ultrasonic inspection system 232 sends ultrasonic energy 234 in the form of ultrasonic beam 236 into object 204 at each location in plurality of locations 238.

Array of transmitting elements 222 is configured to send energy 226 to plurality of locations 238 on object 204.

In one illustrative example, plurality of locations 238 includes locations defined by a grid substantially parallel to plane 211. For example, without limitation, plurality of locations 238 is two-dimensional locations along a grid substantially parallel to plane 211. In some examples, this grid is formed based on wrinkle axis 217 and an axis substantially perpendicular to wrinkle axis 217. Of course, in other illustrative examples, a location in plurality of locations 238 is a three-dimensional location such as, for example, without limitation, a location in x, y, and z coordinates relative to object 204.

Ultrasonic inspection system 232 is moved over outer surface 237 of portion 215 of object 204 to the different locations in plurality of locations 238 according to inspection pattern 235. Inspection pattern 235 may be, for example, without limitation, a raster pattern. When inspection pattern 235 takes the form of a raster pattern, ultrasonic beam 236 is sent into object 204 at each location in plurality of locations 238, one location at a time. Of course, in other examples, inspection pattern 235 may take some other form.

Ultrasonic beam 236 is formed by using array of transmitting elements 222 in a phased manner. In particular, transmitting aperture 242 of array of transmitting elements 222 is used to form ultrasonic beam 236. Transmitting aperture 242 is a subset of array of transmitting elements 222 used to form ultrasonic beam 236. Transmitting aperture 242 includes a number of transmitting elements of array of transmitting elements 222. As used herein, "a number of," when used with reference to items means one or more items. As a result, a number of transmitting elements is one or more transmitting elements. In this manner, transmitting aperture 242 may include one, some, or all of array of transmitting elements 222. In one illustrative example, transmitting aperture 242 is pair of transmitting elements 243. In some illustrative examples, transmitting aperture 242 may also be referred to as a transmitting portion.

In some cases, the same number of transmitting elements of array of transmitting elements 222 is used as transmitting aperture 242 for sending ultrasonic beam 236 into each location in plurality of locations 238. In other cases, different apertures of transmitting elements 222 are used as transmitting aperture 242 for sending ultrasonic beam 236 into different locations in plurality of locations 238.

In one illustrative example, each of the transmitting elements in transmitting aperture 242 may be configured to transmit an ultrasonic pulse at a selected time. This time may be the same or different for the different transmitting elements in transmitting aperture 242, depending on the implementation. The times at which the transmitting elements in transmitting aperture 242 transmit ultrasonic pulses and the strengths of these ultrasonic pulses may be selected such that the waves formed by these ultrasonic pulses combine to form a single wave front that travels at a selected angle relative to object 204. This single wave front forms ultrasonic beam 236. In this manner, array of transmitting elements 222 may be used to electronically steer ultrasonic beam 236 relative to object 204.

For example, ultrasonic beam 236 may be sent into object 204 at location 244 and propagated through object 204. As ultrasonic beam 236 propagates through object 204, at least a portion of ultrasonic beam 236 is reflected off the surfaces of plurality of layers 206 of object 204.

These reflections, which may also be referred to as reflected ultrasonic energy, are received by receiving portion 246 of array of receiving elements 224. Receiving portion 246 includes only two receiving apertures of array of receiving elements 224. As depicted, array of receiving elements 224 has only two receiving apertures configured to receive at least a portion of energy 226 that is reflected off object 204 as reflected energy 228. Each receiving aperture contains a quantity of receiving elements. Each receiving aperture is a subset of array of receiving elements 224.

By having only two receiving apertures of array of receiving elements 224 configured to receive at least a portion of energy 226, the amount of layer data 230 is reduced. By having the amount of layer data 230 reduced, processing time for layer data 230 is reduced. Thus, time for detection of wrinkle 212 and determinations regarding number of dimensions 214 of wrinkle 212 may be reduced.

The only two receiving apertures are referred to as pair of receiving apertures 247. Pair of receiving apertures 247 includes first receiving aperture 248 and second receiving aperture 250. First receiving aperture 248 contains any desirable quantity of receiving elements. In one example, first receiving aperture 248 contains a single receiving element. In other examples, first receiving aperture 248 contains more than one receiving element. Second receiving aperture 250 contains any desirable quantity of receiving elements. In one example, second receiving aperture 250 contains a single receiving element. In other examples, second receiving aperture 250 contains more than one receiving element.

Any desirable quantity of elements is positioned between first receiving aperture 248 and second receiving aperture 250. In some illustrative examples, an even number of elements are positioned between first receiving aperture 248 and second receiving aperture 250. In one example, fourteen elements are positioned between first receiving aperture 248 and second receiving aperture 250. In other examples, less than fourteen elements are positioned between first receiving aperture 248 and second receiving aperture 250. For example, two elements, six elements, or ten elements may be positioned between first receiving aperture 248 and second receiving aperture 250.

Changing the number of elements positioned between first receiving aperture 248 and second receiving aperture 250 changes the angle of reflected energy 228 preferentially detected by pair of receiving aperture 247. The number of elements positioned between first receiving aperture 248 and second receiving aperture 250 is selected to "tune" array of receiving elements 224 to a severity of wrinkle 212.

In some examples, the aperture of transmitting elements sending energy 226 is centered between first receiving aperture 248 and second receiving aperture 250. In these examples, transmitting aperture 242 is centered between first receiving aperture 248 and second receiving aperture 250. By centering transmitting aperture 242 between first receiving aperture 248 and second receiving aperture 250, noise may be canceled out. Specifically, by having first receiving aperture 248 and second receiving aperture 250 equidistant from the aperture of transmitting elements sending energy 226, receiving portion 246 "listens" an equal distance in both directions.

For each layer in plurality of layers 206, the ultrasonic energy in ultrasonic beam 236 reflected off the surface of that layer is received by at least one receiving aperture in array of receiving elements 224. In this manner, receiving portion 246 may receive plurality of reflected signals 245 off plurality of layers 206 in response to ultrasonic beam 236 being sent into object 204 at location 244.

In this illustrative example, plurality of reflected signals 245 may include a reflection off each of plurality of layers 206. However, in other illustrative examples, plurality of reflected signals 245 may include reflections off only some of plurality of layers 206.

Each receiving aperture in receiving portion 246 that receives a reflection may convert that reflection into an electrical signal. Processor unit 225 may be configured to receive the electrical signal formed by each receiving aperture in receiving portion 246 and convert the electrical signal into data that is processed to form location data 252 for location 244.

Location data 252 may include, for example, an amplitude and a time for each of plurality of reflected signals 245 received for location 244. The amplitude may be the amplitude of the reflected signal, while the time may be the time of arrival of the reflected signal. In some cases, this time of arrival may be with respect to the time at which ultrasonic beam 236 was sent into object 204. In one illustrative example, location data 252 includes a data point for each of plurality of reflected signals 245 received in response to ultrasonic beam 236 being sent into object 204 at location 244. The data point for a reflected signal includes at least one of an amplitude value, a time value, an element identifier, a transmitting angle for that reflected signal, or some other type of value.

The element identifier identifies the receiving element in array of receiving elements 224 that received the reflected signal. In some illustrative examples, location data 252 is divided into first aperture data 254 and second aperture data 256. First aperture data 254 is data formed from the reflections received at first receiving aperture 248. Second aperture data 256 is data formed from the reflections received at second receiving aperture 250. The transmitting angle is the angle at which ultrasonic beam 236 was sent into object 204 that resulted in a reflected signal.

Location data 252 for each location in plurality of locations 238 is collected to form layer data 230 for portion 215 of object 204. Processor unit 225 generates layer data 230 for portion 215 of object 204 as portion 215 is being scanned. Portion 215 of object 204 may be considered "fully scanned" once ultrasonic beam 236 has been sent into each location in plurality of locations 238 on portion 215 of object 204.

In these illustrative examples, ultrasonic beam 236 is sent into object 204 at a same selected angle relative to plane 211 at each location in plurality of locations 238. Processor unit 225 may be configured to send layer data 230 to computer system 258 for processing. Computer system 258 uses layer data 230 to generate image 260. In this illustrative example, image 260 represents number of dimensions 214 about wrinkle 212. Image 260 may be used to quantify at least one of shape 216 or size 218 of wrinkle 212.

Layer data 230 may be processed to generate image 260 by identifying difference 262 between first aperture data 254 and second aperture data 256 for each location in plurality of locations 238. Difference 262 is a difference in amplitude of reflections received by first aperture data 254 and second aperture data 256. Difference 262 between first aperture data 254 and second aperture data 256 is affected by plurality of out-of-plane angles 264 associated with wrinkle 212 in portion 215. The more out-of-plane 211 angle 266 is, the greater difference 262 between first aperture data 254 and second aperture data 256. For example, difference 262 is negligible when location 244 is not part of wrinkle 212. Difference 262 is negligible when angle 266 of location 244 is about zero. When angle 266 is about zero, plurality of layers 206 at location 244 are arranged substantially parallel to plane 211.

Difference 262 increases as angle 266 increases. As angle 266 increases, plurality of layers 206 direct reflected energy 228 increasingly preferentially to one of first aperture data 254 or second aperture data 256. Thus, angle 266 may be indirectly determined using difference 262 between first aperture data 254 and second aperture data 256.

In some examples, difference 262 is compared to threshold 268. In these examples, when difference 262 is greater than threshold 268, wrinkle 212 may have undesirable properties.

Difference 262 allows wrinkle 212 to be quantified such that the actual shape 216 and size 218 of wrinkle 212 can be determined within selected tolerances. For example, difference 262 allows width 270 of wrinkle 212 to be determined within selected tolerances. By using difference 262 to determine shape 216 and size 218 of wrinkle 212, shape 216 and size 218 of wrinkle 212 may be more accurately determined. Further, by using difference 262 to determine shape 216 and size 218 of wrinkle 212, shape 216 and size 218 of wrinkle 212 may be more quickly determined.

As depicted, processor unit 272 of computer system 258 processes layer data 230. Processor unit 272 is configured to determine width 270 of wrinkle 212 in object 204 based on reflected energy 228. Processor unit 272 is further configured to determine whether wrinkle 212 is of acceptable quality.

In some illustrative examples, processor unit 272 processes layer data 230 to form image 260. Processor unit 272 may be implemented using hardware, software, firmware, or a combination thereof. When software is used, the operations performed by processor unit 272 may be implemented using, for example, without limitation, program code configured to run on a processor unit, such as processor unit 1304 illustrated below in FIG. 13. When firmware is used, the operations performed by processor unit 272 may be implemented using, for example, without limitation, program code and data and may be stored in persistent memory to run on the processor unit.

When hardware is employed, the hardware may include one or more circuits that operate to perform the operations performed by processor unit 272. Depending on the implementation, the hardware may take the form of a circuit system, an integrated circuit, an application specific integrated circuit (ASIC), a programmable logic device, or some other suitable type of hardware device configured to perform any number of operations.

A programmable logic device may be configured to perform certain operations. The device may be permanently configured to perform these operations or may be reconfigurable. A programmable logic device may take the form of, for example, without limitation, a programmable logic array, a programmable array logic, a field programmable logic array, a field programmable gate array, or some other type of programmable hardware device.

In some illustrative examples, the operations and/or processes performed by processor unit 272 may be performed using organic components integrated with inorganic components. In some cases, the operations and/or processes may be performed entirely by organic components, excluding a human being. As one illustrative example, circuits in organic semiconductors may be used to perform these operations and/or processes.

In this illustrative example, processor unit 272 is implemented within computer system 258. Computer system 258 may be comprised of one or more computers. When more than one computer is present in computer system 258, these computers may be in communication with each other. Processor unit 272 and computer system 258 are considered part of ultrasonic inspection system 232. However, in other illustrative examples, at least some portion of processor unit 272 and/or computer system 258 may be considered separate from ultrasonic inspection system 232. For example, without limitation, at least a portion of processor unit 272 may be implemented remotely.

Image 260 is sent to display 274 of computer system 258. Display 274 is configured to display information to a user. Display 274 may comprise, for example, without limitation, a monitor, a touch screen, a laser display, a holographic display, a virtual display device, and/or some other type of display device. At least one of a user or a computer system may analyze image 260 to determine number of dimensions 214 of wrinkle 212.

Image 260 may take any desirable form. In one example, image 260 is three-dimensional image 276. In another example, image 260 is C-scan 278. C-scan 278 is a two-dimensional depiction of data displayed as a top or planar view. C-scan 278 is either a color image or a greyscale image. Pixel values for C-scan 278 indicate values of the data displayed in C-scan 278.

Three-dimensional image 276 depicts any desirable data related to wrinkle 212. In one example, three-dimensional image 276 is a depiction of difference 262. When three-dimensional image 276 is a depiction of difference 262, three-dimensional image 276 is a first derivative of wrinkle 212. In another example, three-dimensional image 276 is a depiction of an integral of a linearly interpolated fit curve to difference 262. The interpolation is performed across the width of the array and perpendicular to the wrinkle out of plane distortion. In this example, three-dimensional image 276 is a depiction of the profile of wrinkle 212. To create three-dimensional image 276, processor unit 272 may integrate difference 262 to create a wrinkle profile. More specifically, processor unit 272 may interpolate between data points and then perform a discrete integral across the calculation. By interpolating first, the discrete integral will be smoother. The more dense the data, the less smoothing occurs.

Processor unit 272 is configured to determine width 270 of wrinkle 212 in object 204 based on reflected energy 228. Processor unit 272 is further configured to determine whether wrinkle 212 is of acceptable quality.

Processor unit 272 may perform gating on location data 252 or difference 262 to generate C-scan 278. Generating C-scan 278 using an internal sum gate may display wrinkle 212. However, using an internal sum gate may contain additional data not indicative of wrinkle 212. For example, using an internal sum gate may include noise within C-scan 278.

In some illustrative examples, processor unit 272 steps through the thickness of composite object 208 for each location 244 in location data 252. Each step may be referred to as a "slice." Each step or slice is representative of a number of layers within the thickness of composite object 208. Each step may move further into the thickness of composite object 208. By determining difference 262 for each step rather than the full thickness of composite object 208, noise may be reduced. By determining difference 262 for each step rather than the full thickness of composite object 208, wrinkle 212 may be emphasized in C-scan 278.

In some illustrative examples, C-scan 278 is an image of difference 262 over threshold 268 for a single step for all location data 252. In other illustrative examples, C-scan 278 is an image of difference 262 over threshold 268 for a plurality of steps for all location data 252. In these examples, C-scan 278 is a sum of each difference 262 over threshold 268 for the plurality of steps.

The illustration of testing environment 200 in FIG. 2 is not meant to imply physical or architectural limitations to the manner in which an illustrative example may be implemented. Other components in addition to or in place of the ones illustrated may be used. Some components may be optional. Also, the blocks are presented to illustrate some functional components. One or more of these blocks may be combined, divided, or combined and divided into different blocks when implemented in an illustrative example.

In some illustrative examples, processor unit 272 does not process location data 252. In these illustrative examples, processor unit 225 or any other desirable processor unit may process location data 252.

Further, in some examples, display 274 may display an output other than image 260. For example, the output may take the form of at least one of an alert, an ultrasonic A-scan, a report, or any other desirable type of output. An alert may indicate whether wrinkle 212 is an unacceptable quality. A report may include information such as number of dimensions 214 of wrinkle 212.

Figure 3:
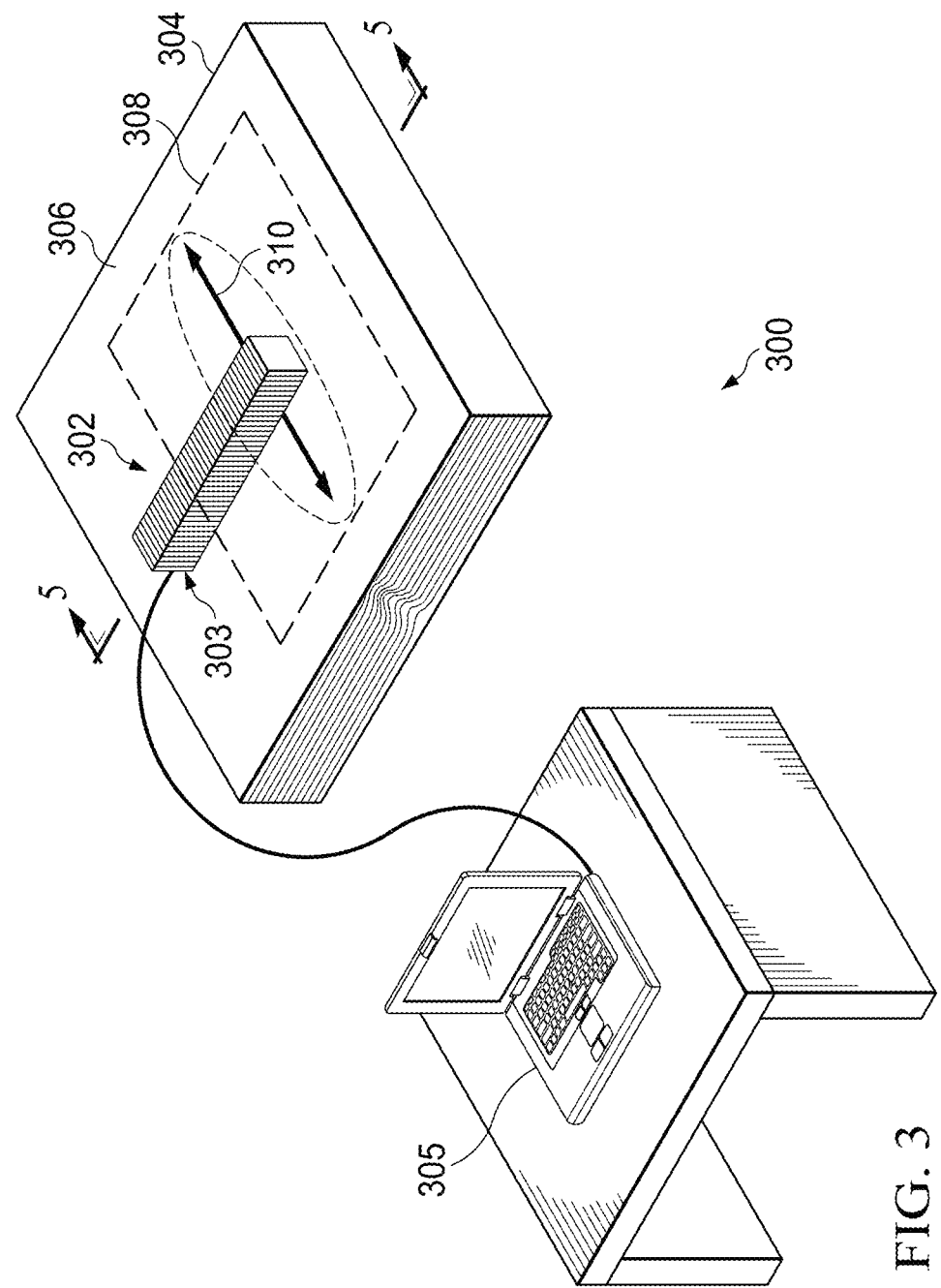
FIG. 3 is an illustration of a testing environment in accordance with an illustrative example.

With reference now to FIG. 3, an illustration of a testing environment is depicted in accordance with an illustrative example. In this illustrative example, testing environment 300 is an example of one implementation for testing environment 200 in FIG. 2. As depicted, in testing environment 300, ultrasonic inspection system 302 is depicted. Ultrasonic inspection system 302 is an example of one implementation for ultrasonic inspection system 232 in FIG. 2.

As depicted, ultrasonic inspection system 302 includes array of elements 303 and computer system 305. Array of elements 303 is configured to function as both an array of transmitting elements and an array of receiving elements. In this manner, array of elements 303 may be an example of one implementation for array of elements 220 in FIG. 2. In this illustrative example, array of elements 303 has been positioned over outer surface 306 of composite object 304.

Composite object 304 is an example of one implementation for composite object 208 in FIG. 2. In this illustrative example, composite object 304 comprises composite layers. A wrinkle in these composite layers has been generally detected within portion 308 of composite object 304. Further, the wrinkle has been identified as extending linearly along wrinkle axis 310. Ultrasonic inspection system 302 may be used to inspect portion 308 of composite object 304 such that the shape and size of the wrinkle may be quantified.

In this illustrative example, array of elements 303 is configured to send an ultrasonic beam into composite object 304 at each of a plurality of locations preselected such that portion 308 of composite object 304 may be raster scanned. Reflected energy that is reflected off the surfaces of the layers in composite object 304 are received by array of elements 303 and converted into electrical signals that are then sent to computer system 305 for processing.

Array of elements 303 is desirably a phased array being scanned along the length of the wrinkle in composite object 304 and across the wrinkle profile. Array of elements 303 desirably has a small pitch to enhance spatial resolution. In some illustrative examples, array of elements 303 may have a pitch of 0.5 mm each.

Turning now to FIG. 4, an illustration of a layout of receiving apertures in an array of elements is depicted in accordance with an illustrative example. View 400 is a cross-sectional view of array of elements 303 in FIG. 3.

In this illustrative example, the individual elements in array of elements 303 may be more clearly seen. Array of elements 303 is an array of ultrasonic transducers in the form of a linear array of ultrasonic transducers configured to send and receive ultrasonic energy. Array of elements 303 may be configured to send energy into a composite object and receive reflected energy. Although array of elements 303 may include any number of elements, in this illustrative example, array of elements 303 includes sixty-four elements.

Array of elements 303 includes transmitting aperture 402. Transmitting aperture 402 has pair of transmitting elements 404. Pair of transmitting elements 404 includes element 406 and element 408. Although transmitting aperture 402 includes two transmitting elements, in other examples, transmitting aperture 402 includes more or less than two transmitting elements.

Array of elements 303 includes receiving portion 410. Receiving portion 410 includes only two receiving apertures configured to receive reflected energy. The only two receiving apertures include a first receiving aperture and a second receiving aperture. Pair of transmitting elements 404 is centered between the first receiving aperture and the second receiving aperture.

In one example, the only two receiving apertures are pair of receiving apertures 412. In this illustrative example, pair of receiving apertures 412 includes first receiving aperture 414 and second receiving aperture 416. As depicted, first receiving aperture 414 includes a single receiving element. In other non-depicted illustrative examples, first receiving aperture 414 includes more than one receiving element. As depicted, second receiving aperture 416 includes a single receiving element. In other non-depicted illustrative examples, second receiving aperture 416 includes more than one receiving element.

In pair of receiving apertures 412, an even number of elements is positioned between first receiving aperture 414 and second receiving aperture 416. Specifically, two elements are positioned between first receiving aperture 414 and second receiving aperture 416.

In another example, the only two apertures are pair of receiving apertures 418. In this illustrative example, pair of receiving apertures 418 includes first receiving aperture 420 and second receiving aperture 422. In pair of receiving apertures 418, an even number of elements is positioned between first receiving aperture 420 and second receiving aperture 422. Specifically, six elements are positioned between first receiving aperture 420 and second receiving aperture 422.

In a further example, the only two apertures are pair of receiving apertures 424. In this illustrative example, pair of receiving apertures 424 includes first receiving aperture 426 and second receiving aperture 428. In pair of receiving apertures 424, an even number of elements is positioned between first receiving aperture 426 and second receiving aperture 428. Specifically, ten elements are positioned between first receiving aperture 426 and second receiving aperture 428.

In a yet further example, the only two apertures are pair of receiving apertures 430. In this illustrative example, pair of receiving apertures 430 includes first receiving aperture 432 and second receiving aperture 434. In pair of receiving apertures 430, an even number of elements is positioned between first receiving aperture 432 and second receiving aperture 434. Specifically, fourteen elements are positioned between first receiving aperture 432 and second receiving aperture 434.

The number of elements positioned between the first receiving aperture and the second receiving aperture may tune array of elements 303 to listen for a particular slope in a wrinkle. For example, increasing the number of elements positioned between the first receiving aperture and the second receiving aperture may increase detection of larger out-of-plane angles.

With reference now to FIGS. 5A and 5B, illustrations of a cross-sectional view of composite object 304 from FIG. 3 are depicted in accordance with an illustrative example. In this illustrative example, a cross-sectional view of composite object 304 from FIG. 3 is taken with respect to lines 5-5 in FIG. 3. As depicted, composite object 304 is comprised of plurality of layers 500. Plurality of layers 500 are an example of one implementation for plurality of layers 206 in FIG. 2.

As depicted, composite object 304 has wrinkle 502. Wrinkle 502 is an example of one implementation for wrinkle 212 in FIG. 2. Wrinkle 502 is formed by a portion of plurality of layers 500. Wrinkle 502 may extend linearly in a direction along wrinkle axis 310 from FIG. 3, which extends through the page in FIGS. 5A and 5B. In response to an ultrasonic beam propagating through composite object 304, at least a portion of the ultrasonic beam is reflected off the surface of each of plurality of layers 500.

The highest-amplitude reflections off the surfaces of plurality of layers 500 form reflected signals corresponding to plurality of layers 500 at the location. When the ultrasonic beam is not directed into composite object 304 at or near wrinkle 502, reflected signals are reflected back in substantially the same amplitude in opposite directions.

Only two apertures in array of elements 303 of FIGS. 3 and 4 are configured at any one time to receive reflected signals from composite object 304. An amplitude and time are generated for each reflected signal received at the only two apertures.

Thereafter, a new location on composite object 304 may be tested by choosing a different portion of array of elements 303 to send an ultrasonic signal into composite object 304. For example, rather than element 406 and element 408 in FIG. 4 in array of elements 303, the elements labeled 408 and 416 may be used to send an ultrasonic beam into composite object 304 at a different location on composite object 304. The ultrasonic beam may be sent into composite object 304 at an angle relative to composite object 304, which may be about 90 degrees relative to composite object 304.

In this manner, different portions of array of elements 303 may be used to send an ultrasonic signal into composite object 304 at different locations on composite object 304. Further, array of elements 303 may be moved over outer surface 306 of composite object 304 such that an ultrasonic beam is sent into composite object 304 at each of the plurality of locations preselected for inspection. In this manner, array of elements 303 may be used to evaluate composite object 304.

In response to the ultrasonic beam propagating through composite object 304, reflected signals are reflected off the surfaces of plurality of layers 500 and received by array of elements 303. Wrinkle 502 may cause reflected signals received by the pair of receiving apertures in array of elements 303 to have different amplitudes.

For a particular location at which an ultrasonic beam is sent into composite object 304, a reflected signal is identified for each layer in plurality of layers 500. The reflected signal is identified as the highest-amplitude reflection received at one of array of elements 303. The amplitude of the reflected signal and the time of arrival of the reflected signal are used to form location data for that particular location. The location data collected for each of the plurality of locations preselected for inspection collectively forms layer data that may be used to form an image of composite object 304 and wrinkle 502 in composite object 304.

In this illustrative example, outline 504 depicts one layer of plurality of layers 500 in wrinkle 502 in composite object 304. Out-of-plane angles of wrinkle 502 are clearly visible in outline 504. As the out-of-plane angles of layer 506 depicted in outline 504 vary, the difference between the amplitude of reflected signals received at the only two receiving apertures will also vary.

Figure 6:
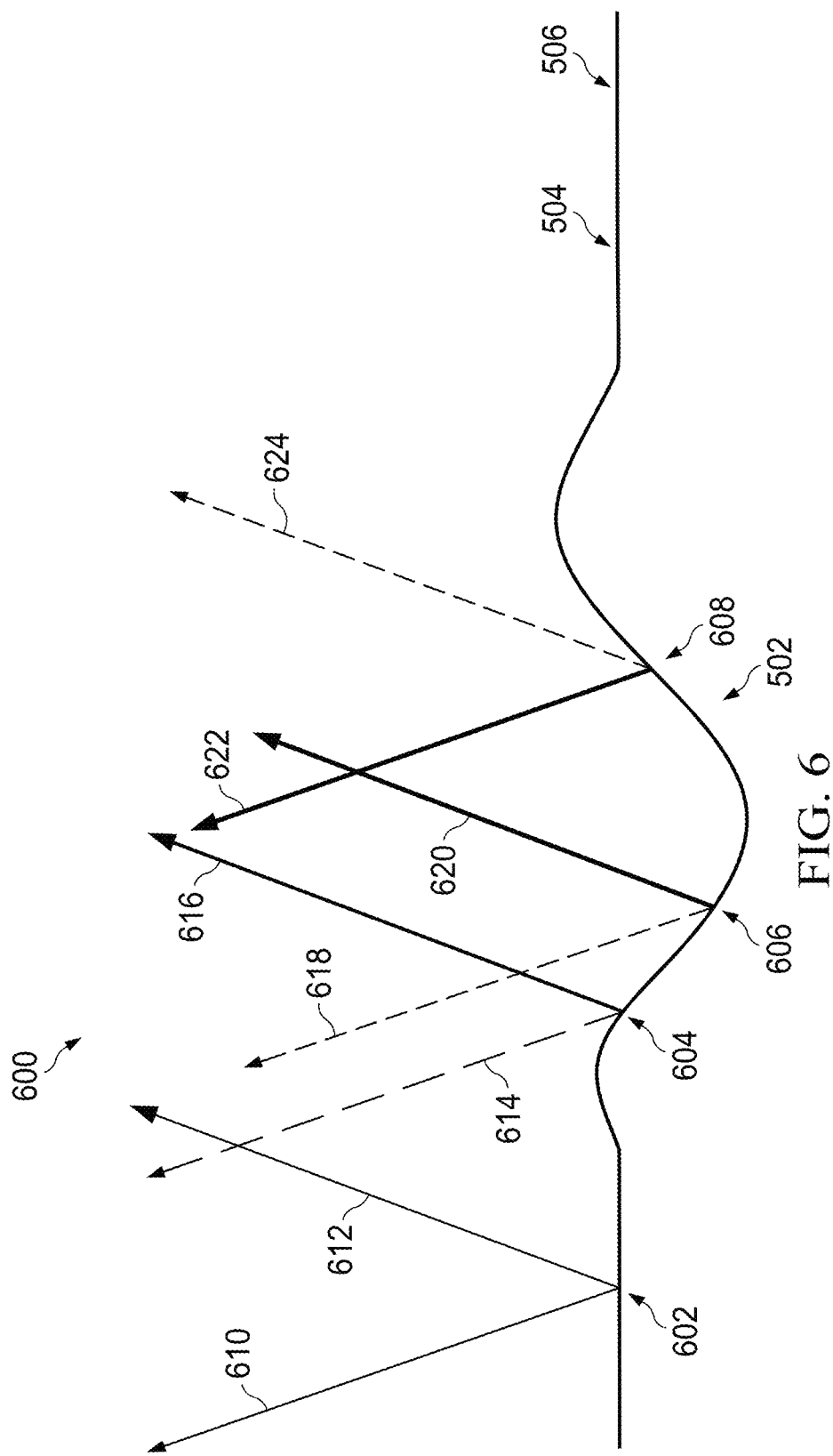
FIG. 6 is an illustration of a cross-sectional view of a composite object in accordance with an illustrative example.

Turning now to FIG. 6, an illustration of a cross-sectional view of a composite object is depicted in accordance with an illustrative example. View 600 is an illustration of a surface of a layer of the plurality of composite layers of the object. In this illustrative example, outline 504 of layer 506 in FIG. 5B is shown for simplification.

During inspection, energy is received at layer 506 at location 602, location 604, location 606, and location 608. Location 602 is not present in wrinkle 502. Location 604, location 606, and location 608 are each positioned within wrinkle 502.

Although only location 602, location 604, location 606, and location 608 are discussed with reference to FIG. 6, this is not limiting. Location 602, location 604, location 606, and location 608 were selected only as illustrative points for discussion. Any desirable number of locations may be inspected along layer 506. Further, the distances between inspected locations may be constant.

As depicted, reflected signal 610 and reflected signal 612 reflect from layer 506 at location 602. Reflected signal 610 and reflected signal 612 have significantly the same amplitude. As depicted, the thickness of reflected signal 610 and reflected signal 612 are substantially the same to demonstrate that reflected signal 610 and reflected signal 612 have significantly the same amplitude.

Reflected signal 614 and reflected signal 616 reflect from layer 506 at location 604. Reflected signal 614 and reflected signal 616 have different amplitudes. As depicted, the thickness of reflected signal 616 is greater than the thickness of reflected signal 614 to demonstrate that the amplitude of reflected signal 616 is greater than the amplitude of reflected signal 614. The difference in amplitude between reflected signal 614 and reflected signal 616 is related to the out-of-plane angle of layer 506 at location 604.

Reflected signal 618 and reflected signal 620 reflect from layer 506 at location 606. Reflected signal 618 and reflected signal 620 have different amplitudes. As depicted, the thickness of reflected signal 620 is greater than the thickness of reflected signal 618 to demonstrate that the amplitude of reflected signal 620 is greater than the amplitude of reflected signal 618. The difference in amplitude between reflected signal 618 and reflected signal 620 is related to the out-of-plane angle of layer 506 at location 606. The out-of-plane angle of layer 506 at location 606 is greater than the out-of-plane angle of layer 506 at location 604. Accordingly, the difference in amplitude between reflected signal 618 and reflected signal 620 is greater than the difference in amplitude between reflected signal 614 and reflected signal 616.

Reflected signal 622 and reflected signal 624 reflect from layer 506 at location 608. Reflected signal 622 and reflected signal 624 have different amplitudes. As depicted, the thickness of reflected signal 622 is greater than the thickness of reflected signal 624 to demonstrate that the amplitude of reflected signal 622 is greater than the amplitude of reflected signal 624. The difference in amplitude between reflected signal 622 and reflected signal 624 is related to the out-of-plane angle of layer 506 at location 608.

As can be seen from FIG. 6, as the degree of an out-of-plane angle increases, the difference in amplitude of reflected energy received at a first receiving aperture and a second receiving aperture increases. Further, portions of outline 504 facing second receiving aperture preferentially direct reflected energy towards the second receiving aperture. Portions of outline 504 facing first receiving aperture preferentially direct reflected energy towards the first receiving aperture.

Figure 7:
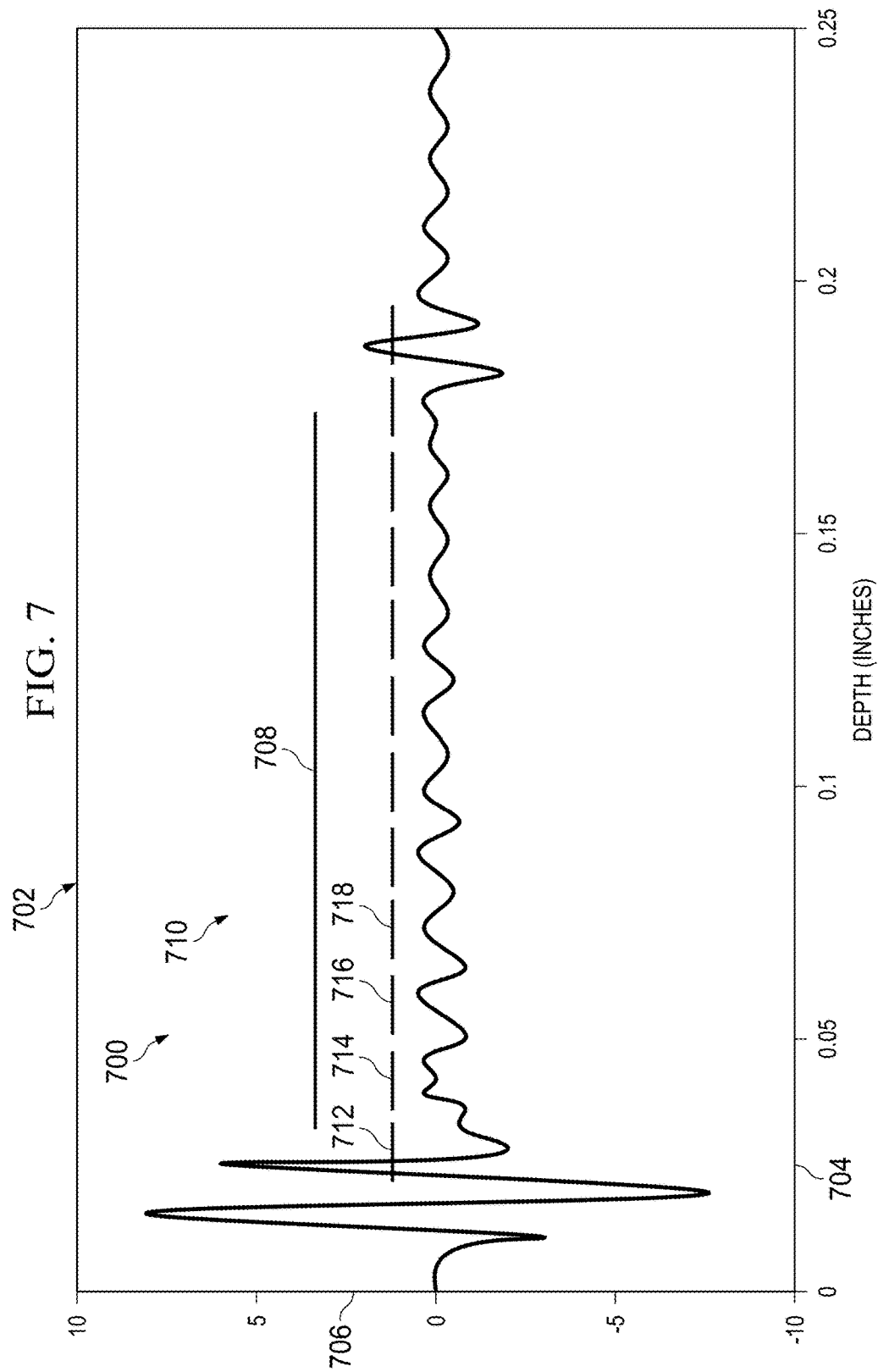
FIG. 7 is an illustration of a graph of received signals in accordance with an illustrative example.

Turning now to FIG. 7, an illustration of a graph of received signals is depicted in accordance with an illustrative example. Data 700 in graph 702 may represent reflected energy 228 from location 244 received at a single receiving aperture of array of receiving elements 224 of FIG. 2.

Graph 702 has x-axis 704 and y-axis 706. X-axis 704 represents depth in inches of the composite structure. Y-axis 706 represents an amplitude of the received response.

Line 708 is indicative of the data processed using an internal sum gate. As depicted, line 708 covers the majority of the received response.

Plurality of lines 710 is indicative of a plurality of steps dividing the received response. Each step of the plurality of steps is processed individually. For example, data within step 712 is processed first. Data within step 712 above a threshold is identified. Data within step 712 above the threshold may be saved. Data within step 714 is processed second. Data within step 714 above a threshold is identified. Data within step 714 above the threshold may be saved.

Data within step 716 is processed third. Data within step 716 above a threshold is identified. Data within step 716 above the threshold may be saved. Data within step 718 is processed fourth. Data within step 718 above a threshold is identified. Data within step 718 above the threshold may be saved. The remainder of steps in the plurality of steps are also processed.

Data in the plurality of steps that is above the threshold may be overlaid. For example, data above the threshold in step 712, step 714, step 716, and step 718 may all be overlaid.

By processing the plurality of steps individually instead of processing all of the data together, noise may be reduced. As a result, by processing the plurality of steps represented by plurality of lines 710 individually, a wrinkle may be easier to identify than by processing all of the data together. Yet further, a width of a wrinkle may be determined by processing the plurality of steps represented by plurality of lines 710 individually. Processing all of the data together may have too much noise to determine a width of a wrinkle.

Figure 8:
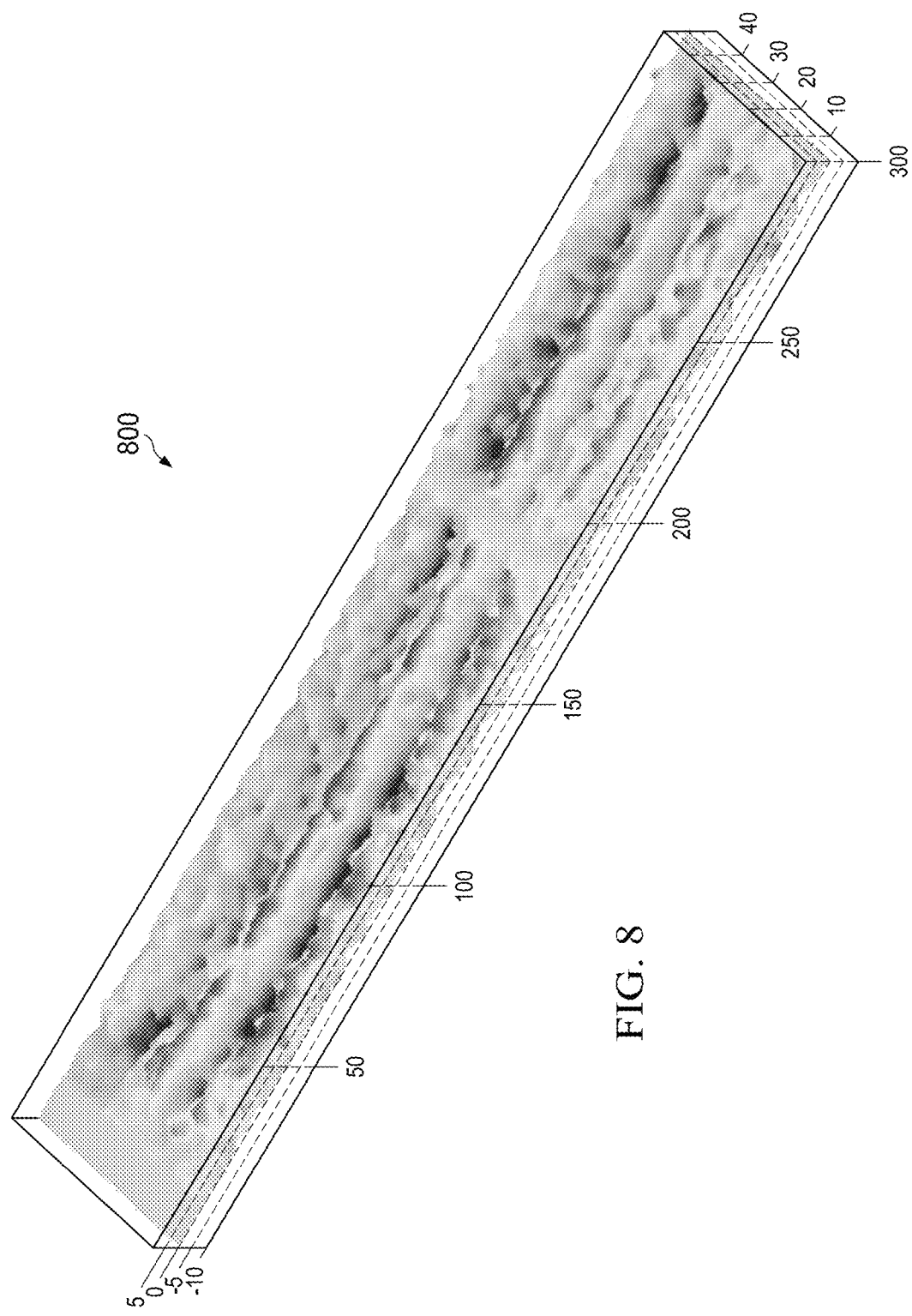
FIG. 8 is an illustration of a surface plot of a difference between a pair of receiving apertures in accordance with an illustrative example.

Turning now to FIG. 8, an illustration of a surface plot of a difference between a pair of receiving apertures is depicted in accordance with an illustrative example. Three-dimensional image 800 is an example of an implementation of three-dimensional image 276 of FIG. 2. Three-dimensional image 800 is an example of an image created after inspecting wrinkle 502 of FIGS. 5A and 5B of composite object 304 of FIG. 3.

Three-dimensional image 800 is a surface plot of the difference in amplitude between first aperture data of a first receiving aperture, such as first receiving aperture 248 of FIG. 2 and second aperture data of a second receiving aperture, such as second receiving aperture 250 of FIG. 2. Three-dimensional image 800 is an implementation of an image of portion 215 of FIG. 2. Three-dimensional image 800 may be described as a first derivative of the wrinkle.

Figure 9:
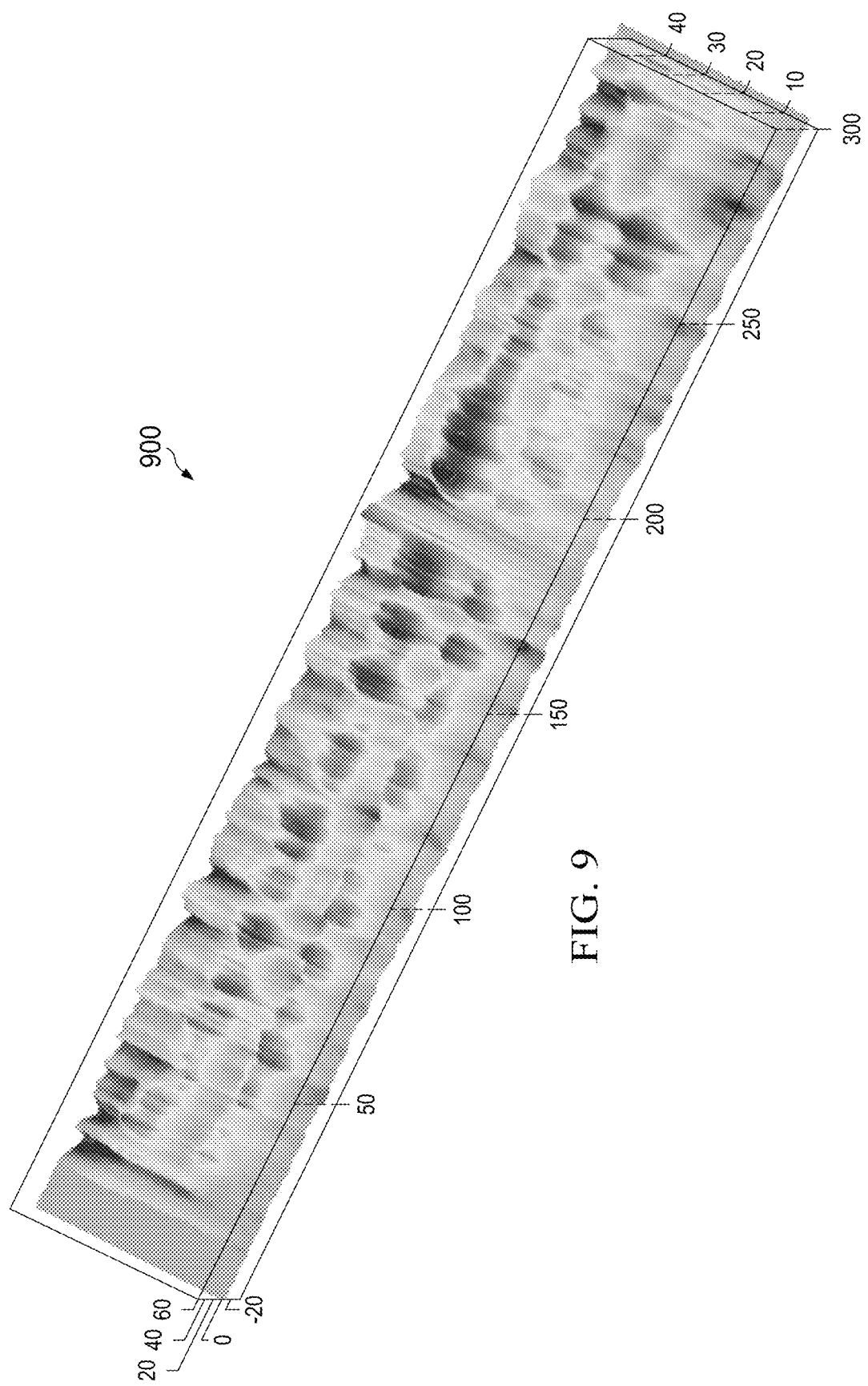
FIG. 9 is an illustration of a surface plot of processed difference data in accordance with an illustrative example.

Turning now to FIG. 9, an illustration of a surface plot of processed difference data is depicted in accordance with an illustrative example. Three-dimensional image 900 is an example of an implementation of three-dimensional image 276 of FIG. 2. Three-dimensional image 900 is an example of an image created after inspecting wrinkle 502 of FIGS. 5A and 5B of composite object 304 of FIG. 3.

Three-dimensional image 900 is a surface plot of an integral of a linearly interpolated fit curve for the difference in amplitude between first aperture data of a first receiving aperture and second aperture data of a second receiving aperture. Three-dimensional image 900 is an implementation of an image of portion 115 of FIG. 1. Three-dimensional image 900 may be described as a profile of the wrinkle.

Figure 10:
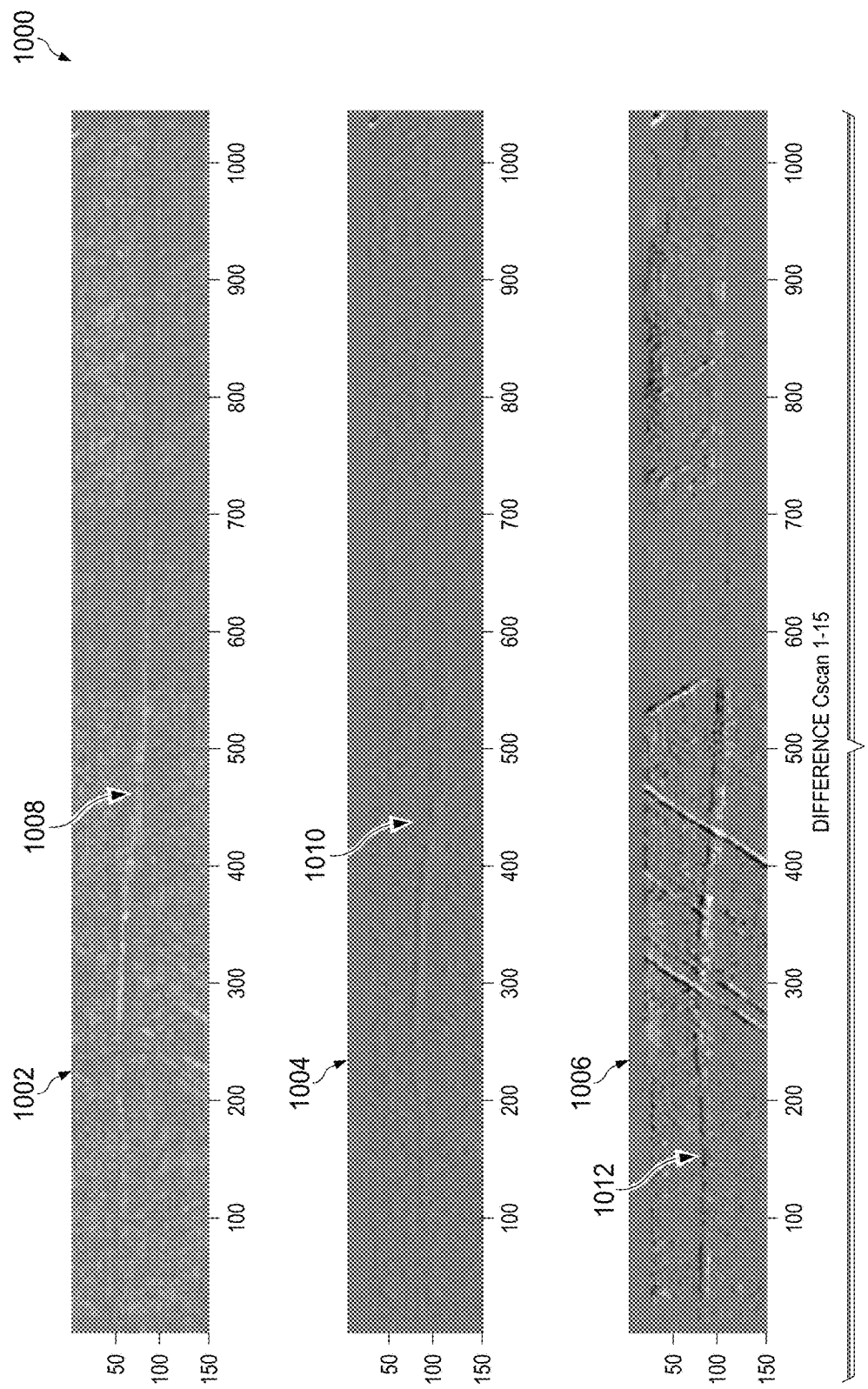
FIG. 10 is an illustration of planar peak data having a number of processing techniques in accordance with an illustrative example.

Turning now to FIG. 10, an illustration of planar peak data having a number of processing techniques is depicted in accordance with an illustrative example. View 1000 includes C-scan 1002, C-scan 1004, and C-scan 1006. C-scan 1002 is an image of planar peak data for one step or slice of the composite object processed using a short max-peak gate with the same transmitting and receiving apertures of the array. C-scan 1002 has indication 1008 of a wrinkle. However, C-scan 1002 has additional noise. Accordingly, characteristics including the width of the wrinkle cannot be determined along the length the wrinkle.

C-scan 1004 is an image of planar peak data for one step or slice of the composite object. For example, C-scan 1004 may be planar peak data for step 714 of FIG. 7. C-scan 1004 depicts differences between the two receiving elements for only this one step. Indication 1010 of a wrinkle is present in C-scan 1004.

C-scan 1006 is an overlay of planar peak data for multiple steps. For example, the history of differences greater than a threshold is overlaid with planar peak data for a current step. For example, C-scan 1006 may be planar peak data for both step 712 and step 714 of FIG. 7. Indication 1012 of a wrinkle is present in C-scan 1006. Indication 1012 is more clearly seen than indication 1008. C-scan 1006 has less noise than C-scan 1002, thus effectively "highlighting" indication 1012. A width of the wrinkle may be determined using indication 1012.

Figure 11:
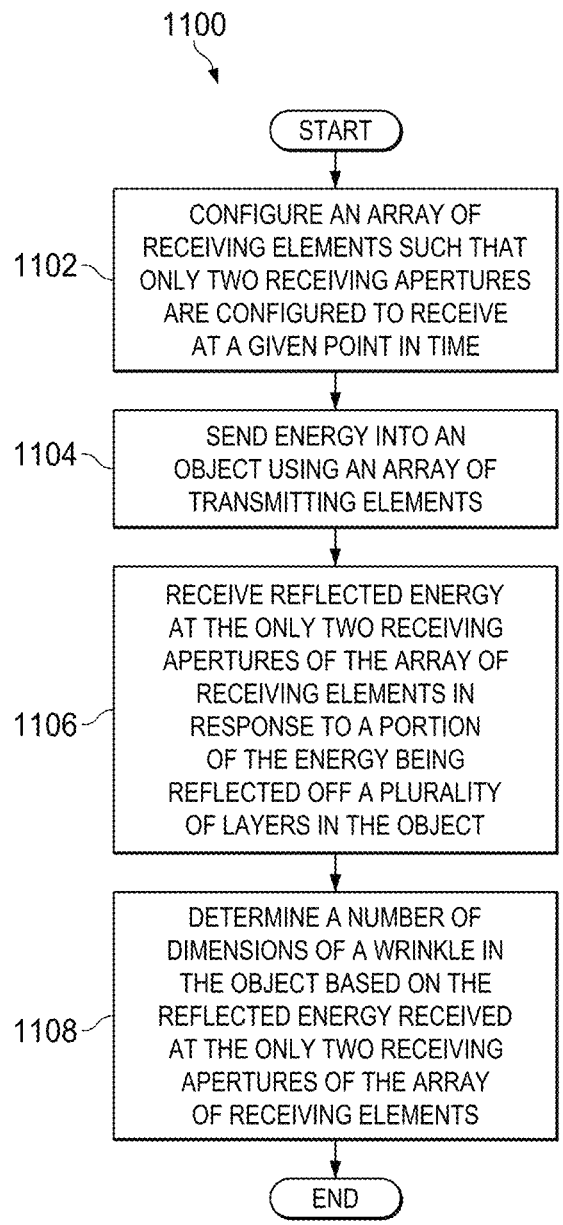
FIG. 11 is an illustration of a process for determining a number of dimensions of a wrinkle in a composite object in the form of a flowchart in accordance with an illustrative example.

Turning now to FIG. 11, an illustration of a process for determining a number of dimensions of a wrinkle in a composite object in the form of a flowchart is depicted in accordance with an illustrative example. Process 1100 may be implemented in inspection system 202 of FIG. 2. Ultrasonic inspection system 232 of FIG. 2 may inspect composite object 208 using process 1100. Ultrasonic inspection system 302 of FIG. 3 may inspect composite object 304 using process 1100. Process 1100 may be implemented to inspect components of aircraft 100 of FIG. 1.

Process 1100 configures an array of receiving elements such that only two receiving apertures are configured to receive at a given point in time (operation 1102). Process 1100 sends energy into an object using an array of transmitting elements (operation 1104).

Process 1100 receives reflected energy at the only two receiving apertures of the array of receiving elements in response to a portion of the energy being reflected off a plurality of layers in the object (operation 1106). Process 1100 determines a number of dimensions of a wrinkle in the object based on the reflected energy received at the only two receiving apertures of the array of receiving elements (operation 1108). Afterwards, the process terminates. In some examples, the number of dimensions of the wrinkle includes a width of the wrinkle.

In some examples, the only two receiving apertures include a first receiving aperture and a second receiving aperture. In these examples, determining the number of dimensions of the wrinkle includes determining a difference in amplitude between the reflected energy received at the first receiving aperture and the reflected energy received at the second receiving aperture.

In some examples, determining a number of dimensions of the wrinkle further includes determining an angle of a layer of the plurality of layers in the object using the difference. In other examples, determining dimensions of the wrinkle further includes: determining if the difference in amplitude is greater than a threshold; and displaying an image of all differences in amplitude for the object greater than the threshold.

Figure 12:
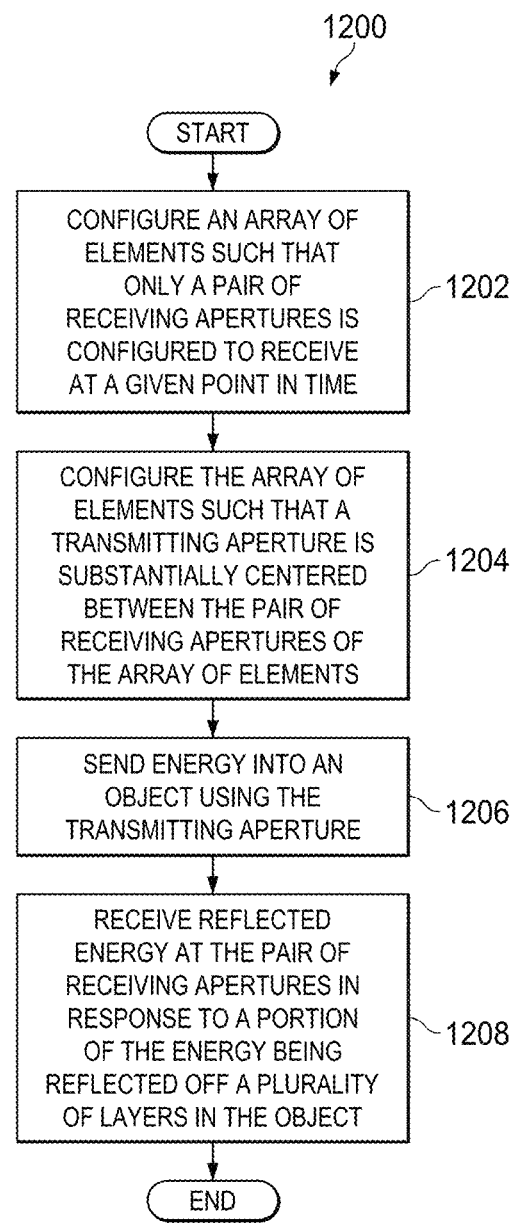
FIG. 12 is an illustration of a process for inspecting a composite object in the form of a flowchart in accordance with an illustrative example.

Turning now to FIG. 12, an illustration of a process for inspecting a composite object in the form of a flowchart is depicted in accordance with an illustrative example. Process 1200 may be implemented in inspection system 202 of FIG. 2. Ultrasonic inspection system 232 of FIG. 2 may inspect composite object 208 of FIG. 2 using process 1200. Ultrasonic inspection system 302 of FIG. 3 may inspect composite object 304 using process 1200. Process 1200 may be implemented to inspect components of aircraft 100 of FIG. 1.

Process 1200 configures an array of elements such that only a pair of receiving apertures is configured to receive at a given point in time (operation 1202). Process 1200 configures the array of elements such that a transmitting aperture is substantially centered between the pair of receiving apertures of the array of elements (operation 1204). Process 1200 sends energy into an object using the transmitting aperture (operation 1206).

Process 1200 receives reflected energy at the pair of receiving apertures in response to a portion of the energy being reflected off a plurality of layers in the object (operation 1208). Afterwards, the process terminates.

In some illustrative examples, the pair of receiving apertures includes a first aperture and a second aperture. In these examples, process 1200 may further include determining a difference in amplitude between the reflected energy received at the first aperture and the reflected energy received at the second aperture.

Process 1200 may additionally include determining if the difference in amplitude is greater than a threshold. Process 1200 may yet further include displaying an image of differences in amplitude from the object greater than the threshold. In some illustrative examples, process 1200 includes determining a width of a wrinkle in the object using the difference in amplitude.

The flowcharts and block diagrams in the different depicted examples illustrate the architecture, functionality, and operation of some possible implementations of apparatus and methods in an illustrative example. In this regard, each block in the flowcharts or block diagrams may represent a module, a segment, a function, and/or a portion of an operation or step.

In some alternative implementations of an illustrative example, the function or functions noted in the blocks may occur out of the order noted in the figures. For example, in some cases, two blocks shown in succession may be executed substantially concurrently, or the blocks may sometimes be performed in the reverse order, depending upon the functionality involved. Also, other blocks may be added in addition to the illustrated blocks in a flowchart or block diagram.

For example, in process 1100, each of the only two receiving apertures includes a single receiving element. In some examples, configuring the array of receiving elements in process 1100 comprises configuring the array of receiving elements such that fourteen elements are positioned between the first receiving aperture and the second receiving aperture of the two receiving apertures.

In some illustrative examples, the array of receiving elements and the array of transmitting elements are a same array of elements. In these examples, process 1100 of FIG. 11 may further comprise configuring the array of transmitting elements such that the energy is sent from a transmitting aperture centered between the first receiving aperture and the second receiving aperture. The transmitting aperture includes any desirable number of transmitting elements. In one example, the number of transmitting elements is a pair of transmitting elements.

Figure 13:
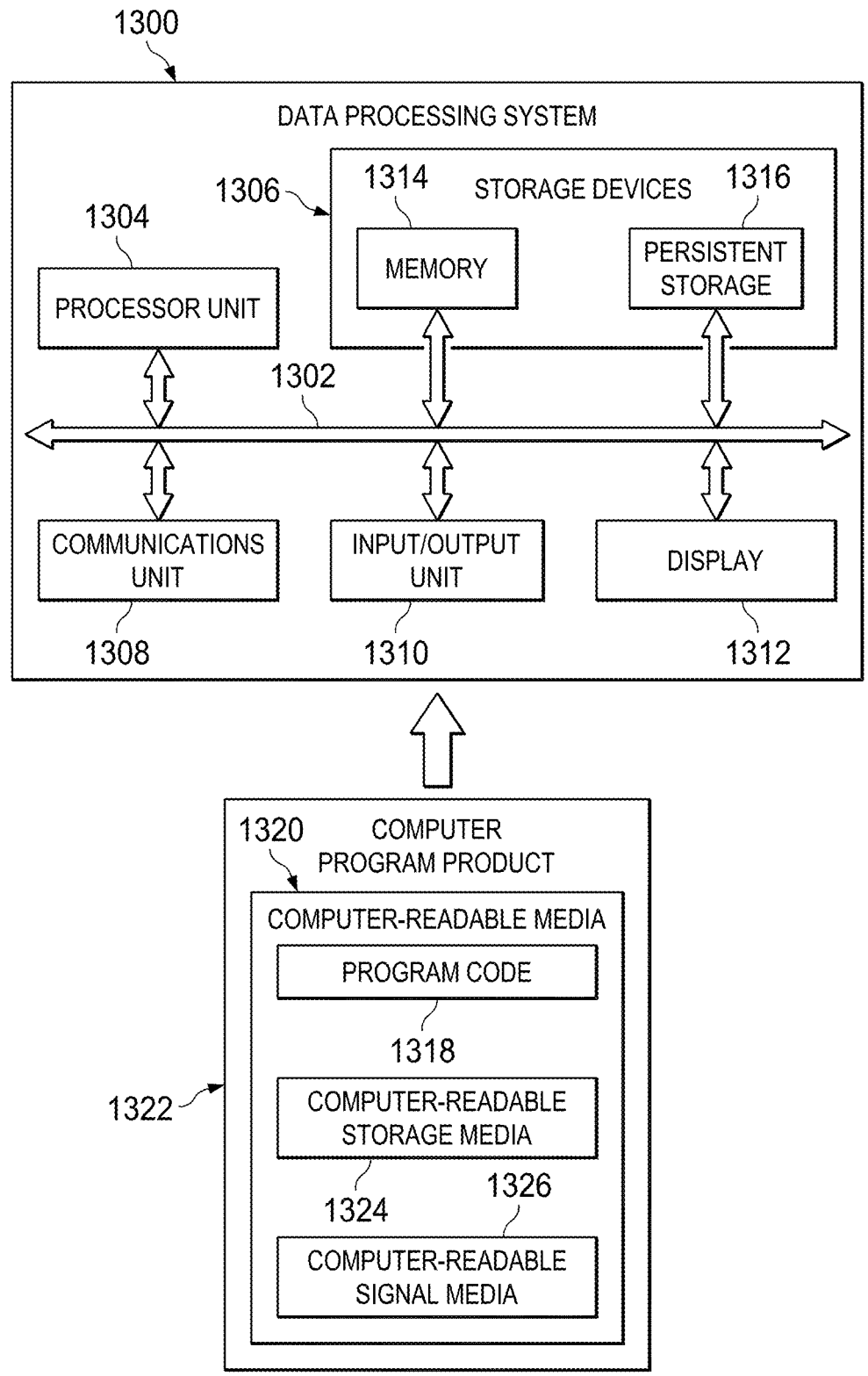
FIG. 13 is a data processing system in the form of a block diagram in accordance with an illustrative example.

Turning now to FIG. 13, an illustration of a data processing system in the form of a block diagram is depicted in accordance with an illustrative example. Data processing system 1300 may be used to implement computer system 258 of FIG. 2. Data processing system 1300 may be used to process data as described in FIG. 3 and display output as depicted in FIGS. 4-8. As depicted, data processing system 1300 includes communications framework 1302, which provides communications between processor unit 1304, storage devices 1306, communications unit 1308, input/output unit 1310, and display 1312. In some cases, communications framework 1302 may be implemented as a bus system.

Processor unit 1304 is configured to execute instructions for software to perform a number of operations. Processor unit 1304 may comprise a number of processors, a multi-processor core, and/or some other type of processor, depending on the implementation. In some cases, processor unit 1304 may take the form of a hardware unit, such as a circuit system, an application specific integrated circuit (ASIC), a programmable logic device, or some other suitable type of hardware unit.

Instructions for the operating system, applications, and/or programs run by processor unit 1304 may be located in storage devices 1306. Storage devices 1306 may be in communication with processor unit 1304 through communications framework 1302. As used herein, a storage device, also referred to as a computer readable storage device, is any piece of hardware capable of storing information on a temporary and/or permanent basis. This information may include, but is not limited to, data, program code, and/or other information.

Memory 1314 and persistent storage 1316 are examples of storage devices 1306. Memory 1314 may take the form of, for example, a random access memory or some type of volatile or non-volatile storage device. Persistent storage 1316 may comprise any number of components or devices. For example, persistent storage 1316 may comprise a hard drive, a flash memory, a rewritable optical disk, a rewritable magnetic tape, or some combination of the above. The media used by persistent storage 1316 may or may not be removable.

Communications unit 1308 allows data processing system 1300 to communicate with other data processing systems and/or devices. Communications unit 1308 may provide communications using physical and/or wireless communications links.

Input/output unit 1310 allows input to be received from and output to be sent to other devices connected to data processing system 1300. For example, input/output unit 1310 may allow user input to be received through a keyboard, a mouse, and/or some other type of input device. As another example, input/output unit 1310 may allow output to be sent to a printer connected to data processing system 1300.

Display 1312 is configured to display information to a user. Display 1312 may comprise, for example, without limitation, a monitor, a touch screen, a laser display, a holographic display, a virtual display device, and/or some other type of display device.

In this illustrative example, the processes of the different illustrative examples may be performed by processor unit 1304 using computer-implemented instructions. These instructions may be referred to as program code, computer usable program code, or computer readable program code, and may be read and executed by one or more processors in processor unit 1304.

In these examples, program code 1318 is located in a functional form on computer readable media 1320, which is selectively removable, and may be loaded onto or transferred to data processing system 1300 for execution by processor unit 1304. Program code 1318 and computer readable media 1320 together form computer program product 1322. In this illustrative example, computer readable media 1320 may be computer readable storage media 1324 or computer readable signal media 1326.

Computer readable storage media 1324 is a physical or tangible storage device used to store program code 1318 rather than a medium that propagates or transmits program code 1318. Computer readable storage media 1324 may be, for example, without limitation, an optical or magnetic disk or a persistent storage device that is connected to data processing system 1300.

Alternatively, program code 1318 may be transferred to data processing system 1300 using computer readable signal media 1326. Computer readable signal media 1326 may be, for example, a propagated data signal containing program code 1318. This data signal may be an electromagnetic signal, an optical signal, and/or some other type of signal that can be transmitted over physical and/or wireless communications links.

The illustration of data processing system 1300 in FIG. 13 is not meant to provide architectural limitations to the manner in which the illustrative examples may be implemented. The different illustrative examples may be implemented in a data processing system that includes components in addition to or in place of those illustrated for data processing system 1300. Further, components shown in FIG. 13 may be varied from the illustrative examples shown.

Figure 14:
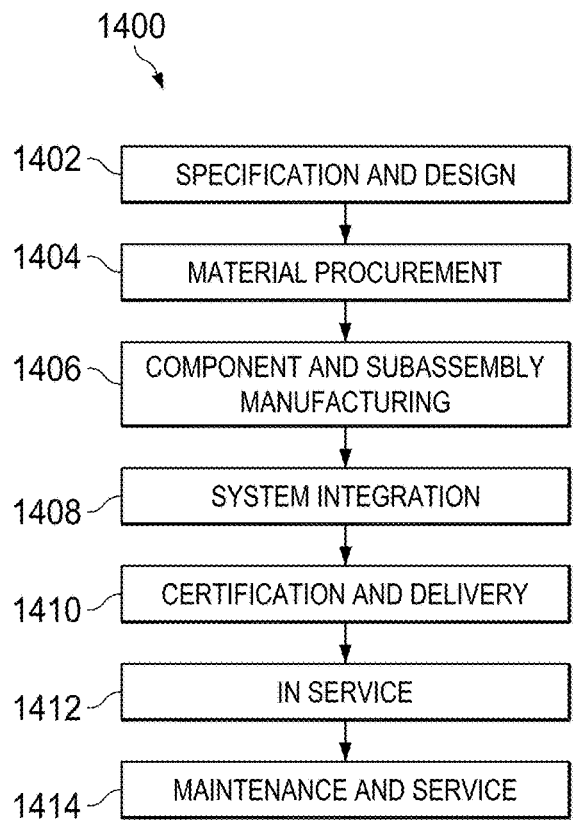
FIG. 14 is an illustration of an aircraft manufacturing and service method in the form of a block diagram in accordance with an illustrative example.
Figure 15:
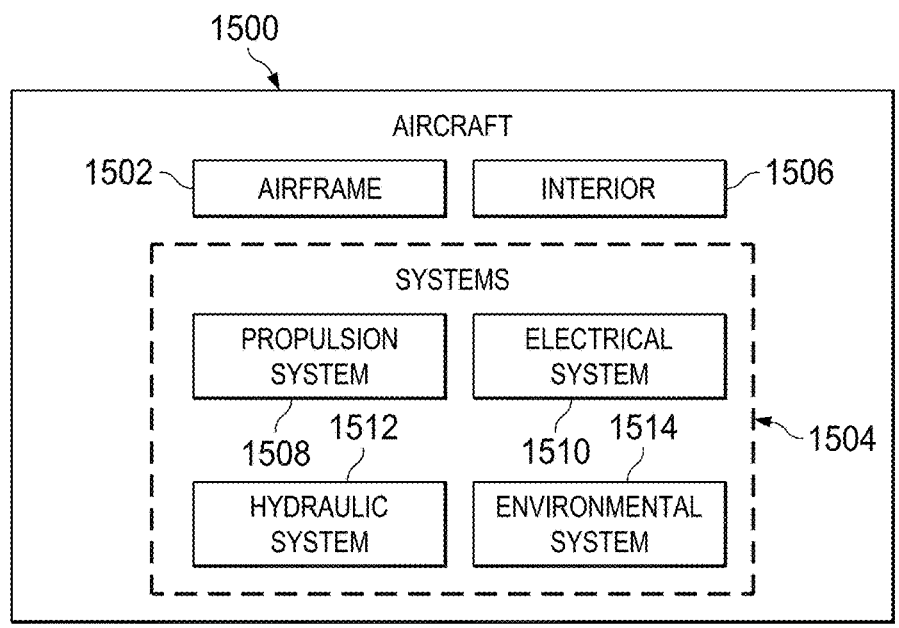
FIG. 15 is an illustration of an aircraft in the form of a block diagram in which an illustrative example may be implemented.

Illustrative examples of the disclosure may be described in the context of aircraft manufacturing and service method 1400, as shown in FIG. 14, and aircraft 1500, as shown in FIG. 15. Turning first to FIG. 14, an illustration of an aircraft manufacturing and service method is depicted in accordance with an illustrative example. During pre-production, aircraft manufacturing and service method 1400 may include specification and design 1402 of aircraft 1500 and material procurement 1404.

During production, component and subassembly manufacturing 1406 and system integration 1408 of aircraft 1500 takes place. Thereafter, aircraft 1500 may go through certification and delivery 1410 in order to be placed in service 1412. While in service 1412 by a customer, aircraft 1500 is scheduled for routine maintenance and service 1414, which may include modification, reconfiguration, refurbishment, and other maintenance or service.

Each of the processes of aircraft manufacturing and service method 1400 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, a leasing company, a military entity, a service organization, and so on.

With reference now to FIG. 15, an illustration of an aircraft is depicted in which an illustrative example may be implemented. In this example, aircraft 1500 is produced by aircraft manufacturing and service method 1400 in FIG. 14, and may include airframe 1502 with plurality of systems 1504 and interior 1506. Examples of plurality of systems 1504 include one or more of propulsion system 1508, electrical system 1510, hydraulic system 1512, and environmental system 1514. Any number of other systems may be included. Although an aerospace example is shown, different illustrative examples may be applied to other industries, such as the automotive industry.

Apparatuses and methods embodied herein may be employed during at least one of the stages of aircraft manufacturing and service method 1400 in FIG. 14. One or more illustrative examples may be used during component and subassembly manufacturing 1406 in FIG. 14. For example, ultrasonic inspection system 232 in FIG. 2 may be used to inspect composite structures during component and subassembly manufacturing 1406. For example, composite structures of aircraft 1500 may be inspected during component and subassembly manufacturing 1406 for aircraft 1500 using ultrasonic inspection system 232 of FIG. 2.

The description of the different illustrative examples has been presented for purposes of illustration and description, and is not intended to be exhaustive or limited to the examples in the form disclosed. Many modifications and variations will be apparent to those of ordinary skill in the art. Further, different illustrative examples may provide different features as compared to other desirable examples. The example or examples selected are chosen and described in order to best explain the principles of the examples, the practical application, and to enable others of ordinary skill in the art to understand the disclosure for various examples with various modifications as are suited to the particular use contemplated.

What is claimed is:

1. A method comprising:
   configuring an array of receiving elements such that only a first receiving aperture and a second receiving aperture are configured to receive at a given point in time;
   sending energy into an object using an array of transmitting elements;
   receiving reflected energy at the first receiving aperture and the second receiving aperture of the array of receiving elements in response to a portion of the energy being reflected off a plurality of layers in the object;
   determining a difference in amplitude between the reflected energy received by the first receiving aperture and the reflected energy received by the second receiving aperture; and
   determining a number of dimensions of a wrinkle in the object based on the reflected energy received by the first receiving aperture and the second receiving aperture of the array of receiving elements.

2. The method of claim 1, wherein determining the number of dimensions of the wrinkle further includes:
    determining an angle of a layer of the plurality of layers in the object using the difference.

3. The method of claim 1, wherein determining dimensions of the wrinkle further includes:
    determining if the difference in amplitduee is greater than a threshold; and
    displaying an image of all differences in amplitude for the object greater than the threshold.

4. The method of claim 1, wherein the number of dimensions of the wrinkle comprises a width of the wrinkle.

5. The method of claim 1, wherein both the first receiving aperture and the second receiving aperture include a single receiving element.

6. The method of claim 1, wherein configuring the array of receiving elements comprises configuring the array of receiving elements such that fourteen elements are positioned between a the first receiving aperture and the second receiving aperture.

7. The method of claim 1, wherein the array of receiving elements and the array of transmitting elements are a same array of elements, the method further comprising:
    configuring the array of transmitting elements such that the energy is sent from a transmitting aperture centered between the first receiving aperture and the second receiving aperture.

8. The method of claim 7, wherein the transmitting aperture is a pair of transmitting elements.

9. An apparatus comprising:
    an array of transmitting elements configured to send energy to a plurality of locations on an object;
    an array of receiving elements having only a first receiving aperture and a second receiving aperture configured to receive at least a portion of the energy that is reflected off the object as reflected energy, wherein the array of receiving elements and the array of transmitting elements are a same array of elements and an even number of elements are located between the first receiving aperture and the second receiving aperture; and
    a processor unit configured to determine a width of a wrinkle in the object based on the reflected energy.

10. The apparatus of claim 9, wherein a transmitting aperture of the array of transmitting elements is positioned between the first receiving aperture and the second receiving aperture.

11. The apparatus of claim 9, wherein the first receiving aperture and the second receiving aperture each contain a single receiving element.

12. The apparatus of claim 9, wherein the processor unit is further configured to determine whether the wrinkle is of acceptable quality.

13. The apparatus of claim 9, wherY the oject is a composite object comprised of a plurality of composite layers.

14. A method comprising:
    configuring an array of elements such that only a first receiving aperture and a second receiving aperture are configured to receive at a given point in time;
    configuring the array of elements such that a transmitting aperture is substantially centered between the first receiving aperture and the second receiving aperture of the array of elements;
    sending energy into an object using the transmitting aperture;
    receiving reflected energy at the first receiving aperture and the second receiving aperture in response to a portion of the energy being reflected off a plurality of layers in the object; and
    determining a difference in amplitude between the reflected energy received at the first receiving aperture and the reflected energy received at the second receiving aperture.

15. The method of claim 14 further comprising:
    determining if the difference in amplitude is greater than a threshold.

16. The method of claim 15 further comprising:
    displaying an image of differences in amplitude from the object greater than the threshold.

17. The method of claim 14 further comprising:
    determining a width of a wrinkle in the object using the difference in amplitude.

\* \* \* \* \*